United States Patent
Eberl et al.

(10) Patent No.: US 8,944,602 B2
(45) Date of Patent: Feb. 3, 2015

(54) INFORMATION SYSTEM AND METHOD FOR PROVIDING INFORMATION USING A HOLOGRAPHIC ELEMENT

(75) Inventors: Roland H. C. Eberl, Starnberg (DE); Matthais Mayer, Munich (DE); Heinrich A. Eberl, Starnberg (DE); David Dickerson, Starnberg (DE)

(73) Assignee: Metaio GmbH, Munich (DE)

( * ) Notice: Subject to any disclaimer, the term of this patent is extended or adjusted under 35 U.S.C. 154(b) by 145 days.

(21) Appl. No.: 13/223,825

(22) Filed: Sep. 1, 2011

(65) Prior Publication Data

US 2012/0008092 A1 Jan. 12, 2012

Related U.S. Application Data

(63) Continuation of application No. 12/646,670, filed on Dec. 23, 2009, now Pat. No. 8,016,421, which is a continuation of application No. 10/551,445, filed as application No. PCT/EP01/11633 on Oct. 8, 2001, now Pat. No. 7,641,342.

(30) Foreign Application Priority Data

| Oct. 7, 2000 | (WO) | PCT/EP00/09840 |
| Oct. 7, 2000 | (WO) | PCT/EP00/09841 |
| Oct. 7, 2000 | (WO) | PCT/EP00/09842 |
| Oct. 7, 2000 | (WO) | PCT/EP00/09843 |
| May 22, 2001 | (WO) | PCT/EP01/05886 |
| Jun. 8, 2001 | (DE) | 101 27 826 |

(51) Int. Cl.
*A61B 3/10* (2006.01)
*G02C 7/02* (2006.01)
(Continued)

(52) U.S. Cl.
CPC ............... *G09G 5/00* (2013.01); *G02B 27/017* (2013.01); *G06F 3/013* (2013.01); *A61B 3/113* (2013.01); *A61B 3/12* (2013.01)
USPC .......................... 351/221; 351/176; 359/639

(58) Field of Classification Search
USPC .................. 351/41–176, 205–206, 210, 221; 359/13–14, 633, 727, 631, 618–619, 359/625, 629–630, 639
See application file for complete search history.

(56) References Cited

U.S. PATENT DOCUMENTS

| 4,968,127 A | 11/1990 | Russell et al. |
| 4,977,509 A * | 12/1990 | Pitchford et al. ............. 701/525 |

(Continued)

FOREIGN PATENT DOCUMENTS

| DE | 19631414 | 2/1998 |
| DE | 19703592 | 8/1998 |

(Continued)

OTHER PUBLICATIONS

Close, D.H., "Holographic Optical Elements", Optical Engineering, vol. 14, No. 5, Sep.-Oct. 1975, 12 pages.

(Continued)

*Primary Examiner* — Dawayne A Pinkney
(74) *Attorney, Agent, or Firm* — O'Shea Getz P.C.

(57) ABSTRACT

An information system and a method for providing information in correlation with light that is incident on an eye includes a holographic element disposed in front of the eye and a device capable of recording optical signals which detects light that is incident on the eye via the holographic element. The device capable of recording optical signals detects light which is diffracted by the holographic element before the light impinges on the eye such that the diffracted light does not enter the eye.

12 Claims, 6 Drawing Sheets

(51) Int. Cl.

| | | |
|---|---|---|
| *G02B 27/12* | (2006.01) | |
| *G09G 5/00* | (2006.01) | |
| *G02B 27/01* | (2006.01) | |
| *G06F 3/01* | (2006.01) | |
| *A61B 3/113* | (2006.01) | |
| *A61B 3/12* | (2006.01) | |

(56) References Cited

U.S. PATENT DOCUMENTS

| | | | |
|---|---|---|---|
| 5,331,149 A * | 7/1994 | Spitzer et al. ............... 250/221 | |
| 5,589,956 A | 12/1996 | Morishima et al. | |
| 5,815,126 A * | 9/1998 | Fan et al. ..................... 345/8 | |
| 5,886,822 A * | 3/1999 | Spitzer ........................ 359/630 | |
| 5,973,781 A | 10/1999 | Moeller et al. | |
| 5,980,041 A | 11/1999 | Strachan | |
| 6,008,781 A | 12/1999 | Furness, III et al. | |
| 6,027,216 A | 2/2000 | Guyton et al. | |
| 6,124,954 A | 9/2000 | Popovich et al. | |
| 6,133,989 A | 10/2000 | Stettner et al. | |
| 6,252,565 B1 | 6/2001 | Hall | |
| 6,313,931 B1 | 11/2001 | Gnaedig et al. | |
| 6,826,452 B1 * | 11/2004 | Holland et al. ............... 700/245 | |
| 6,876,473 B2 | 4/2005 | Drinkwater | |
| 6,982,817 B1 | 1/2006 | Halldorsson | |
| 7,023,536 B2 | 4/2006 | Zhang et al. | |
| 7,038,846 B2 | 5/2006 | Mandella | |
| 7,088,440 B2 | 8/2006 | Buermann et al. | |
| 7,110,100 B2 | 9/2006 | Buermann et al. | |
| 7,113,270 B2 | 9/2006 | Buermann et al. | |
| 7,161,664 B2 | 1/2007 | Buermann et al. | |
| 7,203,384 B2 | 4/2007 | Carl | |
| 7,268,956 B2 | 9/2007 | Mandella | |
| 7,474,809 B2 | 1/2009 | Carl et al. | |
| 7,729,515 B2 | 6/2010 | Mandella et al. | |
| 7,826,641 B2 | 11/2010 | Mandella et al. | |
| 7,961,909 B2 | 6/2011 | Mandella et al. | |
| 2002/0063913 A1 * | 5/2002 | Nakamura et al. ........... 359/15 | |
| 2004/0108971 A1 * | 6/2004 | Waldern et al. .............. 345/8 | |
| 2005/0168437 A1 | 8/2005 | Carl et al. | |
| 2011/0227915 A1 | 9/2011 | Mandella et al. | |
| 2012/0038549 A1 | 2/2012 | Mandella et al. | |
| 2013/0194418 A1 | 8/2013 | Gonzalez-Banos et al. | |

FOREIGN PATENT DOCUMENTS

| | | |
|---|---|---|
| DE | 19728890 | 2/1999 |
| DE | 19934162 | 2/2001 |
| DE | 10127826 | 12/2002 |
| JP | 9 251539 | 9/1997 |
| JP | 11 086005 | 3/1999 |
| JP | 11 139229 | 5/1999 |
| WO | WO 98/05992 | 2/1998 |
| WO | WO 98/13720 | 4/1998 |
| WO | WO 99/03013 | 1/1999 |
| WO | WO 02/31577 | 4/2002 |
| WO | WO 02/31578 | 4/2002 |
| WO | WO 02/31579 | 4/2002 |
| WO | WO 02/31580 | 4/2002 |
| WO | WO 02/33472 | 8/2002 |
| WO | WO 02/097511 | 12/2002 |

OTHER PUBLICATIONS

Form PCT/IPEA/409 w/ English translation (10 pages).
International Search Report dated Mar. 13, 2002 w/ English translation (6 pages).
Billinghurst, M. and H. Kato. "Collaborative Mixed Reality." In Proceedings of the First International Symposium on Mixed Reality (ISMR '99). Mixed Reality—Merging Real and Virtual Worlds, pp. 261-283. Berlin: Springer Verlag.
Fuchs, H. et al. "Augmented Reality Visualization for Laparoscopic Surgery." Proceedings of the 1st International Conference on Medical Image Computing and Computer-Assisted Intervention, Oct. 1998. 10 pgs.
Raskar, R. et al. "The Office of the Future: A Unified Approach to Image-Based Modeling and Spatially Immersive Displays." SIGGRAPH 98, Orlando, Florida, Jul. 19-24, 1998. Computer Graphics Proceedings, Annual Conference Series, 1998, pp. 1-10.

* cited by examiner

INFORMATION SYSTEM AND METHOD FOR PROVIDING INFORMATION USING A HOLOGRAPHIC ELEMENT

CROSS REFERENCE TO RELATED APPLICATIONS

This application is a continuation of U.S. patent application Ser. No. 12/646,670, filed Dec. 23, 2009, and entitled *Information System and Method for Providing Information Using a Holographic Element*, which is a continuation of U.S. patent application Ser. No. 10/551,445, filed Dec. 4, 2006, now U.S. Pat. No. 7,641,342 and entitled *Information System and Method for Providing Information Using a Holographic Element*, which is a U.S. National Stage application of International Patent Application No. PCT/EP01/11633, filed Oct. 8, 2001, and entitled *Information System and Method for Providing Information Using a Holographic Element*, the entire disclosures of which are incorporated herein by reference.

BACKGROUND OF THE INVENTION

The present invention relates to an information system and as well as to a method for providing information using a holographic element, particularly in correlation with a light that is incident on an eye.

STATE OF THE ART

In the European Patent Documents PCT/EP00/09843, PCT/EP00/09840, PCT/EP00/09841, PCT/EP00/09842, which were all filed on Oct. 7, 2000, and German Patent Application DE 101 27 826, which was filed on Jun. 8, 2001, multiple information, projection and recording systems as well as corresponding methods are described which have the object of providing information in a manner adapted to the demands of a seeing person. However, it is difficult to implement such a system or method so cost-effectively that it is accessible to the general public.

In European Patent Document PCT/EP01/05886, multiple methods and devices for adapting an optical system to the viewing direction of the human eye, and pertaining systems for determining the change of the relative position between the optical system and the optical system of the eye are described. These systems useful, for example, in connection with the above-mentioned information, projection and recording systems and corresponding methods. However, here also, it is difficult to implement such a device or method so cost effectively that it is accessible to the general public Similar considerations apply to the device for recording the retinal reflex image and superimposition of additional images according to German Patent Document DE 196 31 414 A1 as well as to the method of improving the optical perception ability by modifying the retinal image according to German Patent Document 197 28 890 A1.

SUMMARY OF THE INVENTION

One object of the present invention is to overcome these disadvantages of the state of the art.

In its most general faun, the information system according to the invention comprises a holographic element and an optical scanning device which records the light incident on an eye by way of the holographic element. Such an information system is called a scanning information system.

As an alternative, the basic information system according to the invention may comprise a holographic element and an optical projection device which projects light into the eye by way of the holographic element. Such an information system is called a projecting information system.

Within the context of the invention, the term "light incident on the eye" comprises light incident in the direction of the eye which, after impinging on the eye, is reflected back by the latter, as well as light incident in the direction of the eye which is recorded or deflected for recording shortly before impinging on the eye and is therefore prevented from the actual impinging on the eye. The light incident in the direction of the eye may be ambient light as well as light which is actively beamed into the eye for the purpose of implementing the invention.

According to the invention, light incident on the eye is recorded by way of a holographic element and/or light is projected into the eye by way of a holographic element. While the light recording is used for obtaining information, the light projection can be used for obtaining information as well as for providing information. The holographic element is preferably disposed in front of the eye. Since the eye is not part of the information system according to the invention, this statement is to be interpreted such that the design of the information system permits a positioning of the holographic element in front of an eye.

The possibilities of obtaining information and the subsequent providing, which according to the invention are covered by the term "providing of information", are described in great detail (several hundred pages) in the abovementioned applications. Accordingly, the "providing of information", in addition to the above reference to the content of those applications, is defined here globally as any providing of information which comprises an eye-related providing of information and/or a providing of information obtained with respect to the eye.

According to the invention, the information can be provided to a human being in a tactile, visual, audible, smellable and/or tastable manner. The information can preferably be offered in a manner which meets the requirements of a seeing person to an extent that so far had not been achieved. This may include that the information can be provided to the human being in a suitable manner, that is, by utilizing one or more of the five senses. However, the information can be provided in any manner and requires no addressee. For example, the information can be provided electromagnetically, mechanically and/or optically to another system or may be emitted by an optical or acoustic output system into the environment.

For a better understanding, a differentiation is made in the specification, if required, between a providing of information or obtaining of information in the primary sense of the invention and a providing of information or obtaining of information in the secondary sense of the invention. A providing of information or an obtaining of information in the primary sense of the invention is "a projection of light into an eye by way of a holographic element" or "a recording of light incident on an eye by way of a holographic element". Any other or additional providing of information and/or any other or additional obtaining of information is called a providing of information or an obtaining of information in the secondary sense of the invention.

According to the invention, the holographic element preferably comprises one or more holographic recordings (which corresponds to a "hologram") of an actual object or of an object virtually emulated by a directly or indirectly computer-controlled exposure of the photo material on which the holographic recording is based, and is thus capable of imitating the refraction, diffraction and/or reflection characteristics of this object to a certain extent under the specific circumstances of the holographic reproduction. In particular, information concerning the three-dimensional topology of the object can thereby be recorded and reproduced.

In this case, it is an advantage that the holographic element does not itself have to have the topology recorded therein in its external shape. For example, a flat holographic element could emulate the refraction, diffraction and/or reflection characteristics of a curved object. Likewise, a curved holographic element could emulate the refraction, diffraction and/or reflection characteristics of a differently curved or flat object. A holographic element can also emulate the refraction, diffraction and/or reflection characteristics of respectively different objects in the case of different wavelengths. Details concerning this topic are contained in Section 2 ("holographic element").

While, in the case of a conventional photographic picture, the intensity (in the case of color photography, as a function of the color or wavelength) of the light incident on the photo material is recorded, the fine grained photo material in the case of a holographic recording records the very fine interference pattern of the light waves incident on the photo material. For this reason, the holographic reproduction, which corresponds to an optical diffraction in the sense of the invention, generally depends considerably on the wavelength, the incidence angle and the phase of the incident light.

Concerning the technique of holographic recording and reproduction as well as the possibilities achievable by means of it and the respective limitations of these techniques, reference is made, for example, to German Patent Documents DE 197 03 592 A1 and DE 197 99 162 A1, as well as to the following books and publications: "Optical Holography: Principles, Techniques, and Applications (Cambridge Studies in Modern Optics)" by Hariharan (ISBN: 0521439655), "Introduction to Fourier Optics)" by Joseph Goodman (ISBN: 0070242542), "Optical Information Processing and Holography" by W. Thomas Cathey, John Wiley & Sons, N.Y. 1974, "Computer Generated Holograms: Techniques and Applications", by Wai-Hon Lee in E. Wolf, Progress in Optics XVI, 1978, and "Topics in Applied Physics, Vol. 20: Holographic Recording Materials", H. M. Smith, Publishers, Springer-Verlag, Berlin 1977, and the publications mentioned therein. The entire content of these books and publications is therefore included in this application by reference.

The propagation of light can be influenced by way of refraction, diffraction and reflection, the appropriate term being considerably dependent on the context. In the preceding section, it was shown that neither a listing of the possible types of propagation change by name, nor the term "light propagation change" permit a brief understandable formulation. In the specification, the term "refraction" or "refract" is therefore used synonymously with the actual generic term "propagation change".

Within the context of the invention, an optical scanning device is any device capable of detecting or recording optical signals for the purpose of obtaining information. (In the remainder of the application, the detecting of light as well as the recording of light is frequently called "light recording" for the purpose simplicity.) Normally, such scanning devices comprise at least one transducer in order to ensure a signal separation, signal intensity or the like sufficient for a possible processing. Thus, the optical scanning device according to the invention could comprise an optical transducer, for example, an optoelectronic device, such as a CCD photosensor, a photomultiplier device or a photo diode or a purely optical device which converts the scanned light into purely optical signals for a further optical and/or photo-electronic processing. Lately, considerable technical progress has been made worldwide with respect to such purely optical devices, so that their commercial use can be expected very soon also within the scope of the invention.

An optical projection device within the context of the invention is any device capable of emitting optical signals or light in a controllable manner. (For reasons of simplicity, the emitting of optical signals as well as the controlled output of light will be called "projection" in the remainder of the application.) The former include, for example, lasers, laser diodes, LEDs, OLEDs, etc. The latter could comprise, for example, a combination of a light source, a modulator, which in technical terms is frequently called a "light valve", and a light guiding arrangement which guides the light generated by the light source to the I modulator. Preferably, the optical projection device itself or in cooperation with another device is capable of projecting light which can be determined with respect to its intensity, propagation direction, polarization, spectral composition, particularly its wavelength, and/or another of its parameters. When the parameters of the light are changed with respect to the time, this is technically called a "modulation".

The propagation of light is typically referred to as a beam. In the application, the recorded or projected light is therefore frequently called a recorded or projected "light beam" or also a "scanning beam" or "projection beam". This is the case particularly when discussing the beam path, the beam diameter, the spectral composition and similar characteristics of the detected or projected light, which are frequently associated with the concept of a light beam.

For the purpose of a guiding or a shaping of the recorded or projected light beam, the optical scanning or projection device according to the invention may have a light guiding device and/or a light shaping device. Examples of such devices, whose differentiation from one another is not always clear, are controllable and non-controllable mirrors, splitter mirrors, acousto-optical modulators, holographic elements, apertures, filters, lenses, optical waveguides, etc.

According to the marginal conditions of the embodiment, several optical transducers, optical projection devices, light guiding devices and/or light shaping devices can be combined with one another as separate units or as an integral unit.

As explained in this specification, the present invention can advantageously be used in connection with the systems, devices and methods described in the following initially described published patent documents: PCT/EP00/09843, PCT/EP00/09840, PCT/EP00/09841, PCT/EP00/09842, DE 101 27 826, PCT/EP01/05886, DE 19631 414 A1 and DE 197 28 890 A1. The present invention can also advantageously be used in connection with the application with the title "Device and Method for Determining the Orientation of an Eye" filed on Oct. 8, 2001 by the applicant of this application. The entire content of these published patent applications or applications is therefore included in this application by reference. In view of the preferred embodiment of the systems or devices disclosed therein, they are, for reasons of simplicity, in the following called "spectacles". The present invention can also be implemented as such an embodiment, in which case, holographic elements can be implemented instead of spectacle lenses or as a coating of the spectacle lenses.

The information system according to the invention can be designed, among other things, as a portable or free-standing system, such as a so-called "palm" device (device portable in the palm of the hand), a device integrated in a helmet, a free-standing examination, treatment, display or operating device or a multipart system, in which modulated infrared light from a remote part of the system is reflected by the eye and is subsequently recorded by a holographic element in order to be able to determine the viewing direction with respect to the remote part of the system.

The invention is explained herein both in general and in connection with a concrete embodiment. Naturally, each individual characteristic of the invention can be combined with every other characteristic, as long as the resulting combination does not lead to a result which a person skilled in the art can immediately recognize as nonsensical. This includes the exchangeability of a characteristic mentioned in the singular for a respective plurality of this characteristic, as long as the possibility of such a singularity or plurality was not explicitly excluded. Those modifications and combinations of the described characteristics which a person skilled in the art would consider part of the idea and extent of the invention are also part of the invention. These statements do not concern the determination of the industrial scope of the invention.

In the present application, characteristics of a method are described where expedient. In this case, a device is always explicitly revealed which is suitable for carrying out the method, such as an appropriately programmed computer; sensors capable of supplying the necessary signals; signal processing devices capable of appropriately processing these signals, etc. It is important to note, moreover, that all described device characteristics can analogously be used in a corresponding process for providing information.

Several additional preferred embodiments and combinations of characteristics of the invention will be briefly explained.

The information system according to the invention is preferably suitable for providing information in correlation with light incident on the eye.

Such a dependence on the light incident on the eye is taken into account according to the invention when determining the information, when providing the information or during both of these inherent processes. For example, the information system receives the information as a function of the recorded light, particularly as a function of determined statements of this recorded light, from an information source, such as a databank, a sensor system, an information network link and/or an analyzing device or causes this information to be determined by the analyzing device. When providing the information, this dependence can be taken into account, for example, in that, by means of a back projection into the eye, the information is superimposed into the seen image such that a time-related, color-related, spatial, contrast-related or other meaningful relationship is established between the information and the seen image. The dependence may particularly consist of the fact that the recorded picture is used for determining the position and orientation of the eyeball, so that an image projected on the eye for the purpose of providing information seems to be stationary when the eye is moving, seems to move along when the eye is moving or seems to move corresponding to a defined course when the eye is moving.

As a result of the preferred correlation between the providing of information and the light incident on the eye, the above-mentioned connection expected by the seeing person exists between what is seen and the provided information.

The optical scanning device preferably is at a fixed angular relationship with respect to the holographic element.

According to an embodiment of the invention, an optical scanning device detects light incident on the eye by way of a holographic element. For the holographic characteristics of the holographic element to be useful according to the invention, among other things, the above-mentioned holographic angular conditions have to be met. This can be promoted by a fixed angular relationship between the optical scanning device and the holographic element.

For achieving this characteristic, the optical scanning device and the holographic element may be mounted, for example, on a uniform fixed frame, such as for spectacles, or on a multipart movable frame whose relevant parts can be fixed with respect to one another, preferably in a predetermined relationship.

The optical scanning device preferably detects light refracted by the holographic element before it impinges on the eye and does not arrive in the eye.

The eye is a highly valuable but not perfect optical system. If the information system according to the invention records, for example, images of the environment via the eye as a partially reflecting element, these images have picture distortions. If, however, light is refracted by the holographic element before it impinges on the eye, this light is not influenced by the optical system of the eye.

The optical scanning device preferably detects light which was at first reflected back from the eye and was then refracted by the holographic element.

In many applications, it is useful to detect light which was reflected back by the eye. For example, the information system according to the invention could scan a retinal reflex image of the ambient light incident on the retina of an eye in the visible spectral range simultaneously with an image of the retinal structures emitting in the infrared range, in order to learn the region of the environment at which the portion of the eye with the sharpest vision is momentarily directed.

An optical scanning device for detecting light from the eye can be simplified by a correspondingly developed light guiding device which is preferably disposed in front of the eye and focuses the light, for example, for the detection. The use of a holographic element as a light-guiding element for the refraction of light reflected back from the eye permits a cost-effective implementation of such a normally complex light guiding device.

Preferably, for detection by the optical scanning device the holographic element refracts light originating from the field of vision of the eye only at several discrete wavelengths in the visible range, before it impinges on the eye and also refracts light reflected back by the eye at a discrete wavelength in the infrared range.

Such an embodiment of the invention would be useful, for example, for recording a relatively distortion-free image of the environment, as well as an image of the retinal structures emitting within the infrared range which is valuable, for example, for the detection of the viewing direction. Because the cornea reflects infrared radiation very well, such arrangement is also very meaningful for the recording of cornea reflex images.

Throughout the specification, data concerning, for example, "refractive characteristics of the holographic element at one or several discrete wavelengths", point to the possibility of adapting the wavelengths of the light projected by the optical projection device or the preferably detected wavelength(s) of the optical scanning device to the light refraction characteristics of the holographic element, or vice-versa. In addition, the light refraction characteristics of the holographic element could be adapted to the application requirements. For example, within the scope of an embodiment of the information system according to the invention as low-light-level spectacles, it would be advantageous for the holographic element to refract light originating from the field of vision assigned to the eye at a discrete wavelength situated in the infrared range, before its impinging on the eye and/or after its reflection by the eye in the direction of a scanning device. In the case of a full-color projection, it would be appropriate for the holographic element to be capable of refracting in the direction of the eye the preferably red, blue and green light which is projected by the projection device.

In the case of a precise coordination of the wavelengths of the light to be refracted and of the light-refracting characteristics of the holographic element, despite the high refraction effect at the wavelengths to be refracted, the holographic element can allow light of other wavelengths to pass through essentially undisturbed. This is particularly advantageous when the holographic element is disposed in front of the eye, because the perception of the field of vision could otherwise be impaired.

The holographic element preferably refracts light originating from the field of vision of the eye at fewer than 20, fewer than 10 or fewer than 5 discrete wavelengths in the visible range, either before it impinges on the eye or after its backscattering because of the eye, for detection by the optical scanning device.

As described above, a holographic element influences only the light incident on it which meets the above-mentioned holographic criteria. It is currently difficult to produce holograms which influence light over a wide spectral range. The invention therefore preferably provides that the holographic element refracts light originating from the field of vision of the eye only at several discrete wavelengths in the visible spectral range. Such a hologram can be produced at low expenditures, for example, by an illumination which is correspondingly repeated at the relevant wavelengths. The effects of the light detection limited as a result of the restricted spectral transmissivity of the light guiding hologram can be compensated or reduced by the corresponding adaptation of the information system to the detectable wavelengths. For example, among other things, by the corresponding processing of the signals obtained from the detected light in the information system, analogous to the principle of a flat-bed scanner which detects only filtered red, green and blue light, a highly valuable color picture of the environment could be obtained. Since analogously a hologram normally represents a very narrow-band filter, it may be meaningful for the holographic element to refract light at more than the conventional three (red, green, blue) wavelengths in the direction of the scanning device in order to be able to obtain, for example, from the detected light, a picture which is as true-to-nature as possible. If, however, too many holographic recordings are captured in a single hologram, this results in a mutual impairment of their effect.

The holographic element preferably refracts light originating from the field of vision of the eye at a discrete wavelength in the infrared range either, before it impinges on the eye or after its backscattering as a result of the eye, for detection by the optical scanning device A detection of infrared light from the field of vision is of interest, for example, for detecting images from the field of vision in darkness, half-light, rain, etc., for example, in an embodiment of the information system according to the invention as low-light-level spectacles or as a driver assistance system.

The holographic element preferably refracts light reflected by the eye only at a discrete wavelength in the infrared range for detection by the optical scanning device Such an embodiment is useful, for example, as an eye tracker system, in which the orientation of the eye is determined by means of a detected infrared cornea reflex image or by means of a detected image of the retinal structures emitting in the infrared range.

The holographic element preferably refracts light of one or several discrete wavelengths, at which the optical scanning device has a high sensitivity.

Such an embodiment makes it possible for the optical scanner to detect as much as possible of the light incident on the holographic element. The optical efficiency of the light-detecting part of the information system is therefore increased. Since the retina reflects only a small percentage of the light incident on it, this embodiment would be advantageous, for example, when scanning a retinal reflex image.

If the holographic element refracts only light of one or several discrete wavelengths, at which the optical scanning device has a high sensitivity, despite a high refraction effect at the wavelengths to be refracted, the holographic element can allow light of other wavelengths to pass in an essentially undisturbed manner. This is particularly advantageous when the holographic element is disposed in front of the eye because the perception of the field of vision could otherwise be impaired.

The holographic element preferably refracts light at several discrete wavelengths such that the refracted light is directed to a common point, and the angle of incidence of the light to this point allows a clear, optionally also wavelength-independent conclusion on the angle of incidence of the light onto the holographic element.

As discussed above, the design of the optical scanning device arid/or additional light guiding devices can generally be simplified if the holographic element contributes to focusing the light incident in the direction of the eye. It is particularly advantageous for the refracted light to be directed to a point common to light of all refracted wavelengths. For example, an optical center of the optical scanning device could then be arranged at this point. However, it is advantageous if the available information concerning the angle of incidence of the light onto the holographic element will not be lost during the refraction or focusing of the light, so that, for example, an image, which typically comprises an assignment between a spatial area and the intensity of the light originating from this area, can be obtained from the detected light. If the available information concerning the angle of incidence of the light onto the holographic element is subjected to no wavelength-dependent change, it is easier for the information system according to the invention to evaluate this information, if necessary.

Details concerning the construction of such a holographic element will be supplied in the discussion of the characteristics according to the invention subdivided according to topics.

As addressed above, the information system according to the invention preferably has an optical projection device which projects light into the eye by way of the holographic element.

Accordingly, a scanning information system may also be equipped with an optical projection device in order for example, to permit an optical scanning of the retinal structures for the purpose of eye tracking; that is, a determination of the orientation of the eye as well as an optical projection of image information into the eye.

A projecting information system may have one or more optical projection devices in order, for example, to protect light into both eyes of a user, or to project different light beams into the eye.

Preferably the light detected by an optical scanning device and the light projected in front of an optical projection device runs in the opposite direction through a common directing lens system and can be focused by the optical scanning or projection device such that their respective beams describe the same path from the eye or into the eye.

As a rule, the use of a common light guiding lens simplifies the system because it typically reduces the number of components, and achieves a constant relationship between the scanning beam and the projection beam. It could, for example, be ensured in this manner that a scanning beam reflected by the retina is detected from the area of the retina which is irradiated by a projection beam while the position of the light guiding lens system is the same.

The optical projection device preferably projects light only at one or several discrete wavelengths in the visible range and/or at a wavelength in the infrared range.

Analogous to the principle of an electrode beam color picture screen, which the phosphorescing of pixels in the primary colors red, green and blue permits a full-color picture. For example, the projection of differently colored light at several discrete wavelengths in the visible range into the eye could permit the perception of a full-color picture. The projection of infrared light could be used, for example, for illuminating structures of the eye for the purpose of scanning without generating a perceptible, possibly disturbing image.

The holographic element preferably refracts the wavelengths of the projected light.

A high optical efficiency of the information system according to the invention can be achieved by selecting the wavelengths of the light projected by the projection device according to the light-refracting characteristics of the holographic element, or vice-versa. As discussed above, by precisely coordinating the wavelengths of the light to be refracted and of the light-refracting characteristics of the holographic element, despite the high refraction effect in the case of the wavelengths to be refracted, the holographic element can allow light of other wavelengths to pass through undisturbed.

If the information system has no optical scanning device or the optical scanning device detects no light by way of the holographic element, it may be particularly advantageous for the holographic element to refract light only at the wavelengths of the projected light.

The optical projection device preferably is in a fixed predetermined angular relationship with respect to the holographic element.

According to an embodiment of the invention, an optical projection device projects light by way of a holographic element onto the eye. If in this case the holographic characteristics of the holographic element are to be advantageously used according to the invention, among other things, the abovementioned holographic angular conditions should be met. A fixed angular relationship between the optical projection device and the holographic element can contribute to meeting these conditions.

For achieving this characteristic, the optical projection device and the holographic element may, for example, be mounted on a uniform fixed frame, such as a fixed spectacle frame, or on a multipart movable frame whose relevant parts can be fixed with respect to one another in a fixed, preferably predetermined relationship.

The holographic element preferably comprises one or more optical markings whose light reflection characteristics can cause the information system by means of a photodetector device to calibrate a projection angle of the optical projection device and/or a light guiding device.

Many applications of the present invention, particularly, for example, the quasi-direct projection of an image sequence onto the retina by the holographic element, require high projection accuracy. If the direction of the projection beam is changed with respect to time by the optical projection device and/or a light guiding device, expediently in many cases it is possible, if necessary, to compare the actual value of the projection direction with the desired value of the projection direction. For determining the actual value of the projection direction, it is possible to use predetermined optical markings whose optical characteristics change, for example, the projected light, such that conclusions on the actual value of the projection direction can be made with respect to one, two or three dimensions by detection of the changed light. Depending on the participation of a light guiding device in the determination of the projection direction, the conclusions with respect the actual value of the projection direction supply conclusions on a projection angle of the optical projection device and/or a light guiding device. In a known manner, this permits, for example, the calibration of the position of a light guiding device. As indicated above, naturally, the light of another liquid source could be used for determining the projection angle or the position of the light guiding device, instead of the projected light.

Preferably, such optical markings may, for example, have reflecting, light-refracting and/or light-absorbing characteristics and any one-, two- or three-dimensional geometrical shape; and are implemented in the holographic element. When correspondingly constructed, a holographic implementation of a marking in the holographic element is cost-effective, optically very valuable and easily reproducible. Furthermore, a flag implemented in the holographic element can be constructed in an angle-selective and/or wavelength-selective manner. Thus, the flags could, for example, refract only infrared light, so that they are not perceivable by a user of the information system according to the invention.

The information system preferably uses the light reflection characteristics of the optical markings for calibrating a scanning angle of the optical scanning device and/or of a light guiding device.

Analogous to the above explanations, optical markings can be used for the calibration of a scanning angle of the optical scanning device and/or a light guiding device. For this purpose, it may be expedient to provide a source of predetermined light, whose light can be detected by way of the optical markings by the optical scanning device instead of a detector.

Preferably, the optical markings are generated such that reflective elements during the creation of the holographic element are imaged in the holographic element such that they beam light of one or several wavelengths, (which corresponding to the predetermined angular relationship with respect to the optical projection device is incident on the holographic element) back along the path of incidence.

For the purpose of a simple detection of the light influenced by the optical markings, it is advantageous for the markings to direct the light originating from a defined light source to a common point. As a result, it is advantageous, particularly in the case of embodiments of the invention in which the projection device is to be considered as a point light source, for the optical marking to beam the light originating from the direction of the projection device, at least partially back along the path of incidence. Thus, this light, which was beamed back, could then be detected by a detector device, optionally the optical scanning device, arranged confocally with respect to the projection device.

The photo detector device preferably has a splitter mirror which is arranged such in the light beam of the optical projection device that it directs a portion of the light impinging against the projection direction on the splitter mirror in the direction of a photodetector, which detects in at least two areas situated concentrically around one another.

A confocal arrangement of the optical projection device and of a photodetector device (optionally, the optical scanning device) can be implemented in a particularly simple manner by arranging a splitter mirror symmetrically directly in front of the optical projection device and the photodetector device.

By means of a detector arrangement, which detects in at least two areas situated concentrically around one another, it can be determined whether an incident light beam is moving in the direction toward or away from the detector center. This can be used advantageously for the calibration of the light guiding components of the information system.

The holographic element preferably has light-refracting characteristics at one or several discrete wavelengths, which correspond to a reflection on the concave side of an area constructed according to the curvature of a rotationally symmetrical ellipsoid.

If the eye is considered to be an idealized optical system, in which incident light always runs through a common optical center, and if the optical output of a projection device or a light guiding device coupled thereto and/or the input of a scanning device or of a light guiding device coupled thereto are considered to be a point light source or a point detector, beams originating from one of the points would always run to the other point if these points correspond to the respective focal points of an internally reflecting rotationally symmetrical ellipsoid.

By means of a holographic element, the reflection characteristics of such an ellipsoid can be emulated without requiring that the holographic element has the external shape of such an ellipsoid. Furthermore, by means of the knowledge of the shape of the ellipsoid, from the angle of incidence of the light on the detector point, the "angle of reflection" of the light from the eye can be determined, or from the projection direction, the angle of incidence on the eye can be determined.

The holographic element preferably has light-refracting characteristics at one or several discrete wavelengths which correspond to a refraction on the concave side of an area constructed according to the curvature of a rotationally symmetrical ellipsoid. Such refraction corresponds to reflection at a respective conical area that is rotationally symmetrical about the axis of rotation of the ellipsoid and is perpendicular to the ellipsoid at the site of the refraction.

If the eye is considered to be an idealized optical system, in which incident light always runs through a common optical center, and if the input of a scanning device or a light guiding device coupled thereto is considered to be a point detector, beams directed at the one point would always run through the other point if these points correspond to the respective focal points of as above described rotationally symmetrical ellipsoid of a holographic element implemented in such a manner. By means of the knowledge of the shape of the ellipsoid, the "angle of incidence" of the light onto the eye can be determined from the angle of incidence of the light on the detector point.

While such a holographic element would be difficult to implement by the holographic recording of a real object, such a holographic element can be implemented by computer-controlled exposure. The result is an easily reproducible optical element capable of refracting light beams directed onto an eye while maintaining a clear assignment to the angle of incidence onto a common point. In addition, by means of a holographic element, the indicated refraction characteristics can be emulated without any effect on the external shape of the holographic element.

A special advantage of an embodiment of the holographic element described here (for the purpose of the present explanation: "HE 1") is its possible combination with a holographic element ("HE2") according to the preceding section. If the respective ellipsoids are uniform and virtually identical with respect to location, and HEI is used, for the refraction of light beams ("L1 beams") incident directly from the environment, while HE2 is used for the refraction of light beams ("L2 beams") between the eye and the projecting or light-detecting components of the information system, those L1 beams directed at HE1 and those L2 beams directed at/from HE2 are coaxial which have the same beam path between HEI or HE2 and the respective projection, scanning or light guiding device. This advantage will be explained in detail below with reference to the drawings.

Individual characteristics of the invention will be discussed in the following. For the purpose of clarity, the discussion of the characteristics is subdivided according to topics.

1 Operating Modes

Initially, the phrase "providing of information" according to the invention was globally defined as any providing of information which comprises an eye-related providing of information and/or a providing of information obtained with respect to the eye. This includes particularly the projection of optical information onto the eye as well as the optical determination of the orientation of the eye.

Many embodiments of the information system according to the invention require, for example, an at least partial image of the field of vision assigned to the eye and/or an at least partial image of selected eye structures, such as the color of the iris or structure of the vessels of the retina, in order to provide information in the intended manner. In many embodiments of the information system according to the invention, several sources of information carrying and/or information-supplying optical signals are used in order, for example, to establish a correlation between different information or in order to obtain redundant information. Such images and/or other optical signals that are valuable for providing information can be obtained or generated, for example, in the following manner.

Since the information system according to the invention projects and/or detects light by way of a holographic element, a holographic element preferably arranged in front of the eye is required as a light guiding element in this section ("Operating Modes") of the specification. However, this should not be understood to be a restriction. If the described scanning or projection takes place in the secondary sense of the invention, this secondary scanning or projection can be implemented without a holographic element or even without a light guiding device.

1.1 Detection of Light from the Eye

The invention provides three preferred approaches for obtaining light signals from the eye: passive point-focal scanning, scanning at an active point focal illumination and point-focal scanning at an active planar illumination. Other types of scanning, which are not considered to be preferable, will be discussed at the end of this section.

Devices for the scanning of light were discussed in detail at the beginning. In the approaches described in the following for obtaining light signals from the eye, the detected light beam is preferably refracted by means a holographic element which is preferably arranged in front of the eye.

1.1.1 Passive Point-Focal Scanning

For the passive point-focal scanning of light from the eye, ambient light serves as the light source. This type of scanning is therefore suitable for detecting retina and cornea reflex images of the environment or also the color of the iris. However, here, ambient light is also the light which, for example, the structures inherent to the body radiate. These include, for example, the infrared light emitted by the structure of retinal or scleral vessels. These structures can therefore also be detected by means of this type of scanning.

A point-focal, as it were, pixel-by-pixel scanning of the eye takes place takes place serially according to the invention. In this case, respective selected areas of the eye are scanned successively in a targeted manner. This preferably takes place by means of a light guiding device, for example, by a corresponding focusing and/or a corresponding spatial limitation of the detected light beam by means of a corresponding focusing, superimposing, scanning and/or other conventional light guiding devices, known to a person skilled in the field of scanning devices.

A further selection of the scanned area or light can take place, for example, by way of a time-related, color-related or other limitation of the detected light.

When the design of the optical scanning device or possibly that of the light guiding device is appropriate, the point-focal scanning has the advantage that, when impinging on the holographic element, the detected light beams have a small diameter and therefore, in the event of an uneven virtual shape of the holographic element, suffer no significant distortions, whereas, in the case of wide light beams, different portions of the light beam may be refracted very differently by the holographic element. (Concerning the difference between the shape of the holographic element and the virtual shape of the holographic element, reference is made to the above description as well as to Section 2 "Holographic Element".

In passive scanning, the dependence of the detectable light on the environmental conditions, that is, on the available ambient light, is a disadvantage. This represents a problem mainly when detecting visible light from the environment at night or in half-light. Furthermore, it may lead to difficulties when scanning a retina reflex image because the retina reflects only approximately 4% to 10% of the incident light.

With respect to the characteristics of the holographic element, the passive point-focal scanning of light from the eye requires that the holographic element is capable of refracting in the direction of the scanning or light guiding device those light beams coming from the eye which are to be detected. Here, it should be taken into account that holograms, as discussed above, normally have their refraction effect only in the case of a few predetermined relatively narrow spectral ranges. This is disadvantageous when detecting, for example, retina or cornea reflex images of the environment which typically comprise numerous spectral components. Some preferred embodiments of the invention therefore provide that the holographic element refracts light at several discrete wavelengths, for example, 5, 10 or even 20.

In the case of the passive detection of monochrome images, for example, infrared images of the structure of vessels of the retina, the abovementioned characteristic of holographic elements is unproblematic because the holographic element can be designed for refracting light of the relevant wavelength.

In the case of the passive point-focal scanning of light from the eye, a holographic element is preferably used which has light-refracting characteristics at one or several discrete wavelengths which correspond to a reflection on the concave side of an area constructed according to the curvature of a rotationally symmetrical ellipsoid.

1.1.2 Scanning at Active Point-Focal Illumination

In the case of this advantageous type of scanning, the regions of the eye to be examined are actively illuminated in a point-focal and successive manner by a projection device, while the light reflected by the respective region is detected by the scanning device. (As described in Section 1.5, the light radiated from the respective region of the eye can also be detected simultaneously from the or a scanning device).

Here also, the respective regions of the eye, as discussed above, are illuminated or scanned successively in a targeted manner preferably by means of a corresponding light guiding device. It is interesting, however, that, at a correspondingly high illumination in comparison to the available ambient light, in the above-mentioned sense, a considerable spatial limitation of the detected light will not be necessary without eliminating a quasi-point-focal scanning. The reason is that, in such a case, the scanning device predominantly detects light which has been reflected back by the targeted region of the eye, which corresponds to a point-focal scanning.

A differentiation between the projected and reflected-back light and the ambient light can be achieved, for example, by means of a modulation. This could, for example, comprise an amplitude modulation during which the intensity of the projected light is changed several times during the projection of a respective pixel so that the "firm" fraction of ambient light in the detected light can be estimated on the basis of the relative changes of the detected light occurring because of the modulation. Similarly, the projected light could be characterized by the time-related change of its polarization, its wavelength or of another one of its parameters such that it can be differentiated from the ambient light. Many signal separation methods usable for this purpose are known to a person skilled in the field of signal processing.

A configuration of the information system according to the invention, as described above, in which a considerable spatial limitation of the detected light is eliminated, could lead to a simplification of the scanning device or of the light guiding device and could be used, for example, in the case of an eye tracker, where imperceptible infrared light (of an intensity which is harmless but strong compared to the ambient light) is beamed into the eye for tracking eye movements.

It is also interesting that, in the case of a scanning of the retina by using active point-focal illumination, the iris acts as an aperture which predominantly allows the light to radiate from the eye, which has been reflected approximately parallel to the illumination beam back from the retina. For this reason, in this type of scanning, a confocal arrangement of the scanning device and of the projection device is preferred.

Also in scanning at an active point-focal illumination, because of the narrow point-directed light beam, there is little distortion of the light beam by the holographic element. However, such a scanning does not suffer from the disadvantages of a passive scanning.

With respect to the implementation of the holographic element, the scanning at an active point-focal illumination offers considerable advantages. The main reason is that the wavelength of the light emitted by the projection device can be adapted to the light refracting characteristics of the holographic element, or vice-versa. Since the reflected-back fraction of the light projected by the projection device forms the basis of the scanning, the holographic element would therefore also be adapted to the wavelength of the light to be detected.

When scanning at an active point-focal illumination, a holographic element is preferably used that has light-refracting characteristics at one or several discrete wavelengths, which correspond to a reflection on the concave side of an area constructed according to the curvature of a rotationally symmetrical ellipsoid.

1.1.3 Point-Focal Scanning at an Active Planar Illumination

In this type of scanning, the regions of the eye to be examined are actively illuminated in a planar manner by means of a projection device, while respectively selected point-focal regions of the eye, as discussed above, are preferably successively scanned in a targeted manner by means of a corresponding light guiding device. Thus, for example, ocular structures can be when sufficient ambient light is not available for such a scanning. However, a scanning of an ocular reflex image of the environment is not possible because the detected light does not originate in the environment.

Because of the active illumination, as described in the previous section, here also a differentiation can be achieved between the projected and reflected-back light and the ambient light, for example, by means of a modulation.

Likewise, there is the advantage of an adaptation of the wavelength of the projected or detected light to the light refraction characteristics of the holographic element, in which case the illumination or projection and/or the scanning can take place by way of the holographic element.

A disadvantage of this type of scanning are the high demand on the scanning device and the light guiding device possibly assigned to it, in order to carry out a targeted scanning. An information system constructed in this manner benefits from the fact that the holographic element causes no significant distortions in the case of a narrow point-directed scanning beam, as it would be the case with a wide beam.

During the point-focal scanning at an active planar illumination, a holographic element is preferably used which has light-refracting characteristics at one or several wavelengths, which correspond to a reflection on the concave side of an area constructed according to the curvature of a rotationally symmetrical ellipsoid.

1.1.4 Other Types of Scanning

Naturally, there is also the possibility of a planar (that is, parallel instead of serial) scanning. The method of operation of such a scanning is well known and does not have to be explained here in detail.

However, it should be pointed out here that the planar scanning in connection with the shape of compact spectacles preferred by the invention, in the case of a cost-effective construction, normally results in undesirable optical distortions, which is why this embodiment is considered to be secondary.

1.2 Confocal Detection of Light Quasi-Directly from the Environment

The information system according to the invention detects light incident on the eye by means of an optical scanning device. As discussed above, this light according to the invention does not actually have to impinge on the eye but may also simply have been directed at the eye before it is detected by the information system or directed to the detection.

A particularly advantageous embodiment of the information system according to the invention has a device which permits a detection of light confocal to the eye directly or quasi-directly from the environment. In this manner, an image of the perceived field of vision can, for example, be obtained which is free of distortions by the optical system of the eye. Different such devices are easily conceivable by any person skilled in the art and are also described in detail in the European Patent Applications PCT/EP00/09840, PCT/EP00/09841 and PCT/EP00/09843, which is why a repetition of these data will not be necessary here.

However, according to the invention, a detection of light preferably confocal to the eye can take can quasi-directly from the environment, that is, without any diversion by way of the eye, by means of the holographic element. The latter is preferably arranged in front of the eye. A special advantage of the use of a holographic element for the refraction of light is the fact that its refraction characteristics, as described above, are not exclusively determined by its external shape but also in that its refraction can be designed in a precise, easily reproducible, wavelength-selective and/or angle-selective manner.

According to a preferred embodiment of the invention, for this purpose, the holographic element has the above-described light-refracting characteristics at one or several discrete wavelengths, which correspond to a refraction on the concave side of an area constructed according to the curvature of a rotationally symmetrical ellipsoid, which refraction corresponds to a reflection at a respective conical area rotationally symmetrical about the axis of rotation of the ellipsoid which, at the site of the refraction, which conical area is perpendicular to the ellipsoid at the site of the refraction.

In such an embodiment, the input of the scanning device or of a light guiding device coupled thereto has to be situated at one of the focal points of the ellipsoid and face the holographic element in order to detect the ambient light refracted by the holographic element. If, in addition, measures are taken which provide that the other focal point of the ellipsoid coincides approximately with the optical center of the optical system of the eye, those light beams are detected which, confocally with respect to the optical system of the eye are incident on the holographic element from the environment. Such measures may, for example, comprise the possibility of mechanically or manually adjusting the position of the holographic element, possibly together with the optical scanning device and/or light guiding device.

1.3 Projection

As discussed above, a projection according to the invention can be used when obtaining information from the eye as well as providing information. Devices for the light projection were discussed in detail at the beginning.

A narrow light beam and/or the holographic element are preferably used for the projection, which holographic element has light-refracting characteristics at one or several discrete wavelengths, which preferably correspond to a reflection on the concave side of an area constructed according to the curvature of a rotationally symmetrical ellipsoid, and/or which is preferably arranged in front of the eye. The advantages of additional advantageous further development possibilities of such a holographic element were described above.

1.3.1 Projection for Obtaining Information

During the projection for obtaining information, light is projected by a projection device such that it can be reflected and can be detected for the purpose of obtaining information. For obtaining information with respect to the eye, the light is projected onto the eye and reflected by it.

Two significant implementations of such a projection were described above under the headings "Scanning at an Active Point-Focal Illumination" and "Point-Focal Scanning at an Active Planar Illumination". Likewise, the eye could be actively illuminated in a planar manner and could be scanned in a planar manner. According to the implementation, these types of projection can be used in the primary sense or in the secondary sense of the invention.

In the secondary sense of the invention, other types of projections in connection with corresponding scanning methods could be used in a meaningful manner. For example, light could be projected on a part of the information system or into the environment according to one of the described projection or scanning methods, could be reflected there and could finally be detected by the information system. Such an obtaining of information could, for example, be used for calibrating the optical components of the information system or for obtaining information from the environment.

During the projection for obtaining information, the projected light is preferably modulated or characterized in a different manner in order to be able to, for example, differentiate this light from the ambient light. A modulation may, for example, also be used to determine the transit time of the light between the projection device and the scanning device.

Furthermore, infrared light is preferably projected during the projection for obtaining information in order not to impair the scenery perceived by the person.

1.3.2 Projection for Providing Information

Basically any projection of light corresponds to a transmission, that is, to a providing of information.

In the primary sense of the invention, information is provided by means of a projection in that optical information in the form of light is projected into the eye by way of a holographic element. So that the information is perceivable by the eye, the light is projected onto the retina. So that the light can transmit the desired optical information, the light is subjected to a corresponding modulation. For example, light is projected in an intensity modulated manner at a red, a blue and a green wavelength pixel-by-pixel such that, as a result of the well-known principle of color addition, the light is perceived as a full-color picture.

According to the logical final conclusion of the two preceding sections, a projection for providing information in the secondary sense of the invention comprises any other or additional projection of light. For example, the information system according to the invention may project light that is later scanned by the information system itself and is analyzed for the purpose of a calibration or an adjustment. Likewise, light could be projected into the environment in order to be perceived there directly or indirectly by a person or to be detected by another system.

The use of a holographic element as a light guiding device during the projection offers, among other things, the advantage that the refraction characteristics of the holographic element can be adapted to the wavelength of the projected light, or vice-versa. This could be used, for example, for guiding visible light from a projection device into the eye, while infrared light from the same projection device is guided into the environment for the purpose of controlling another system.

While the serial as well as the parallel projection of light can be used for providing information, the serial pixel-by-pixel projection is preferred because it permits the use of a very narrow light beam whose beam shape remains essentially unchanged during a refraction on a curved or virtually curved area. (Concerning the interpretation of the term "virtually curved", reference is made to Section 2 "Hologram").

1.4 Detection of the Environment by Means of a Sensor System

The information system according to the invention preferably has a sensor system which preferably supplies information with respect to the environment.

As was described in detail in the International Patent Documents PCT/EP00/09840, PCT/EP00/09841 and PCT/EP00/09843, it may be very advantageous for the information system according to the invention to have a sensor system for the detection of environmental data. Such environmental data can, for example, be used for determining the position and orientation of the information system and/or of the eye with respect to the environment. Likewise, environmental data can be used for providing information in correlation with the light incident on the eye.

In the following, two of these sensor systems will be briefly discussed which can be used in a particularly advantageous manner for providing information in correlation with light incident on an eye.

1.4.1 Camera

The information system according to the invention preferably has a camera.

The detection of light from the environment by way of a camera, for example, a CCD camera, offers a cost-effective possibility for detecting highly valuable optical signals from the environment. The optical picture taking axis of the camera should coincide as closely as possible with the optical axis of the eye in its neutral, that is, forward-looking position, in order to supply a picture which is almost confocal with the eye and is therefore, in comparison with the perceived picture, essentially parallax-free.

If the picture recorded by the camera is partially or entirely compared with reflex images of the environment obtained from the eye, the region of the environment "targeted" by the eye can be precisely determined, for example, from the relationship of the reflex images with respect to simultaneously detected structures of the eye.

1.4.2 Position Sensor System

The information system according to the invention preferably has a position sensor system.

As a rule, by way of the knowledge of the optical characteristics of the components of the information system according to the invention, the beam path of a scanned light beam can be precisely determined. Thus, by means of a corresponding analysis of information obtained from the eye, the orientation of the eye with respect to the components of the information system can also be determined in a precise manner.

By means of a position sensor system integrated in the information system, for example, an IR or RF triangulation device, a GPS receiver, and/or gyrosensors, which cooperates, if required, with remote components, such as fixedly positioned transmitters, satellites or the like, the position and/or the orientation of the information system can be determined. As a result, the position and/or orientation of the eye with respect to the environment can also be determined. Naturally, such a position sensor system can also serve other purposes within the scope of providing or obtaining information.

1.5 Mixed Operation

As initially mentioned, the above-described methods for providing or for obtaining information can be arbitrarily combined.

A particularly advantageous embodiment of the information system according to the invention detects optical signals from the environment by means of an ellipsoid-type holographic element according to Section 1.2, which refracts light at 1-5 wavelengths, as well as by means of a camera according to Section 1.4.1. In addition, it detects information concerning the structure of the retina by means of optical signals in the infrared range according to Section 1.1.2 by way of an also ellipsoid-type holographic element. As a result of the identical design and position of the ellipsoids as well as an identical beam path between the holographic element and the scanning device, it is achieved that an advantageous coaxial relationship, as initially described, exists between the light beams detected from the eye or the light beams detected from the environment by way of the scanning device. By means of a suitable comparison of patterns of the redundantly detected information from the environment, a precise relationship can also be determined between the information in each case detected from the environment. Thus, for example, the viewing direction of the eye with respect to the environment can be precisely determined in a simple manner.

The advantages of the described embodiment are that the holographic element has to comprise few (in a borderline case, two) holographic recordings, that no optically highly valuable scanning device is required since the spatial limitation of the scanned area can take place by means of the projection, and that the projection used for obtaining information can take place in the not perceivable infrared range.

The above-described example describes only one of the countless combination possibilities and therefore is used essentially for exemplifying the conceivable advantages of an information system implemented in the "mixed operation".

In particular, it should be pointed out that the combinations of a projection and/or detection of visible light and of a projection and/or detection of not perceptible infrared light can lead to particularly advantageous embodiments of the invention. In this case, several wavelengths of the respective type of light can also be used. As mentioned above, a projection and/or detection by way of a holographic element permits an adaptation of the light-refracting characteristics of the holographic element to the wavelengths of the light to be projected or to be detected.

1.6 Flying Spot

Scanning and projection methods by which spatially limited regions are serially scanned or illuminated typically along a straight or curved line, in technical terminology, are frequently called "flying-spot" methods.

In the case of many conventional eye-related information systems, optical signals are detected in a planar manner by means of a flat detector from the eye, or are projected into the eye in a planar manner by means of a flat projector. This approach has the disadvantage that an optically correct imaging of a curved part of the eye on a flat detector or of a flat projector onto a curved part of the eye can be achieved only at considerable expenditures.

This problem occurs to a considerably reduced extent when the flying-spot method is used.

In addition, because of its compatibility with a holographic element, the flying-spot method is preferably used in the case of the information system according to the invention.

1.6.1 Spiral, Circular or Ellipsoid Scan

The human mono-ocular perception is essentially rotationally symmetrical about a visual axis extending through the fovea centralis and the optical center of the lens. Correspondingly, many parts of the eye, for example, the iris, the pupil, the cornea, the lens in some respects, also the retina, in most people, are constructed approximately rotationally symmetrically about the visual axis.

According to the invention, therefore, preferably according to the flying-spot method, the eye will scan with a spiral-shaped, or circular scanning or projection pattern, preferably about the visual axis, in which case, "circular" may be a plurality of concentric circles. If the projection beams or scanning beams are situated correspondingly diagonally with respect to the visual axis, the use of an ellipsoid scanning or projection pattern may be advantageous, as described in German Patent Document DE 197 28 890 A1.

It should be stressed that the term "scanning or projection pattern" here should be understood to be the quasi two-dimensional movement pattern described by the starting or end point of the beam path of the light detected from the eye by the scanning device or of the light projected into the eye by the projection system.

1.6.2 Beams Perpendicular to the Eye

If the light beams are incident perpendicular on the air-eyeball transition, a certain fraction of the light is reflected back into the opposite direction with respect to the incident light beam, while the residual fraction beams through quasi unhindered, after which it is absorbed or scattered by deeper-lying parts of the eye. The former analogously applies to light beams exiting from the eye by way of the cornea-air transition.

In the case of the information system according to the invention, the projecting or scanning preferably takes place according to the flying-spot method. In this case, a "narrow" light beam is preferably used which has an insignificant diameter at the air-eyeball transition in comparison to the eyeball curvature, particularly the curvature of the cornea. Likewise, a light beam with a "narrow" diameter can be used according to Section 3.1 "beam diameter". The light beam is preferably projected or scanned such that all its individual rays encounter the air-eyeball transition as perpendicularly as possible.

The cornea, that is, the air-cornea transition, causes approximately 80% of the refraction exercised by the eye upon an incident light beam. The above-described approach therefore not only has the advantage that little light at the air-cornea transition is refracted into a useless direction but also has the advantage that the beams experience a slight refraction by means of the optical system of the eye. This has a positive effect not only on the spatial projection or scanning precision but is also advantageous in applications in which the geometry of the light beams plays an important role. This is the case, for example, in eye tracker applications.

The fact that beams perpendicularly incident on the eye are partially reflected back in the opposite direction can be used for obtaining information concerning the topology of the eye. This can take place, for example, by means of a projector—detector arrangement which comprises a projection device and a scanning device and projects light approximately perpendicularly onto the eye, and subsequently determines the co-axiality of the detected reflected-back light beam and of the projected light beam. If these light beams are not essentially coaxial (particularly the cornea surface has many micro- and macroscopic irregularities and therefore should not be considered to be a smoothly reflecting surface), it can be concluded that the projected light beam was not perpendicularly incident on the eye. Such information concerning the topology of the eye can, among other things, be used for determining the position and/or orientation of the eye.

A confocal arrangement of the projection device and of the scanning device, for example, by way of a splitter mirror, is useful for such a projector-detector arrangement.

A scanning device which is advantageous in this context and has concentric detector ranges is described in Section 3.4 ("Special Scanning Devices").

The use of a holographic element is advantageous particularly during the projection and the detection of a light beam extending perpendicular to the eye, because it permits a simple virtual further development (compare Section 2 "holographic element") of a complex light guiding device, such that light beams from several or even a single projection device can be directed perpendicularly onto different areas of the eye, and/or light beams exiting or reflected back perpendicularly from different areas of the eye can be directed into several or even a single scanning device.

Such a holographic element can be produced, particularly by computer-aided methods. Hardly any limits exist with respect to the design. In principle, it is only necessary that the beam path of a beam situated perpendicular to the eye leads by way of the holographic element to a projection device, a scanning device and/or to a light guiding device coupled therewith. When designing the holographic element, it is preferably provided that the angle of incidence or reflection of the beam on the scanning devices, the projection devices and/or the light guiding device coupled therewith permits clear conclusions on a respective region of the eye to be assigned to the beam; that is, that the angle of incidence or reflection of the beam at the scanning device, the projection device and/or a light guiding device coupled therewith represents a clear image of respective regions of the eye, and vice-versa.

Since the eye is not round and, in addition, pivotable, a light guiding device, particularly a holographic element, which is always capable of directing projection beams perpendicularly onto any exposed region of an eye (or inversely for scanning beams) can hardly be implemented. In particular, it is problematic that the eye typically does not pivot about a point which coincides with the center of the curvature of the cornea. The light guiding device is therefore preferably designed according to an empirical model of the region of an eye to be detected with the assumption that the eye is normally within a certain rotating range. As an alternative, the light guiding device can be designed as a good approximation according to a model of a spherical eye obtained from empirical data.

2 The Holographic Element

The holographic element plays a decisive role for the present invention as the light guiding device. The basic characteristics of the holographic element were described at the beginning. Particularly, the capability of a holographic element of imitating the refraction characteristics of an object to a certain extent and under the specific circumstances of the holographic reproduction was stressed there.

Illustrated in an extremely simplified manner, a hologram can be considered to be a recording of the interference pattern of two light beams, specifically of an object beam and of a reference beam. If light corresponding to the reference beam is incident on the finished hologram, it is "converted" by the refraction characteristic of the interference pattern to a light beam corresponding to the object beam. Typically, the object beam corresponds to the light refracted by a real object. Correspondingly, by illuminating the hologram by means of the reference beam, the light refracted by a real object can become quasi visible in the absence of this object. The object becomes, as it were, "virtually" visible. In this manner, the hologram "virtually" imitates the shape, that is, the refraction characteristics of the object.

In this case, it is advantageous that the physical shape of the hologram, which is typically implemented in the manner of a foil or as a coating, does not at all have to coincide with the shape of the recorded object; that is, with the "virtual" shape of the hologram. Correspondingly, the virtual shape of the hologram is freely selectable according to the system requirements. However, differences in the shape of the holographic photo material between the recording and the reproduction influence the interference pattern and thus also the reproduction. If required, this should be taken into account correspondingly.

The electro-holographic elements, which are also part of the group of holographic elements, should also be mentioned. Electro-holographic elements are holographic elements whose holographic content can change by applying a voltage. With respect to the production and the precise operation of electroholographic elements, reference is made to the pertinent technical literature.

2.1 Production Method

The production of holograms is a very complex operation whose exact description would exceed the scope of this application. At the beginning, several published examples concerning this topic were therefore mentioned by name.

The production of holograms can be divided into two basic categories. These are the computer-aided production and the holographic recording of a real object. One typical example of these manufacturing methods respectively will be briefly described in the following.

2.2.1 Real Object

The information system according to the invention preferably has a holographic element comprising a holographic recording of a real object. A holographic element can be most easily produced by means of a holographic recording of a real object. In this case, a reference beam quasi directly originating from the light source and an object beam refracted at the real object are normally projected simultaneously onto the holographic photo material. Since the sharp recording of an interference pattern requires a "holding still" the interference pattern for the duration of the recording, normally laser beams are used as the object beam and the reference beam. So that only one laser light source is required, the laser beam originating from the laser light source can be divided into two parts by means of a splitter mirror, one part directly beaming on the photo material and the other indirectly beaming on the photo material by way of the object.

In this manner, time-invariant light guiding devices, such as mirrors, diffusing plates, lenses and the like, can be holographically recorded, that is, emulated by way of a holographic element.

2.1 Computer-Aided Production

The information system according to the invention preferably has a holographic element fabricated by means of computer-aided production.

A holographic element produced with the aid of a computer is typically defined and produced by way of its interference pattern. In this case, a fictitious object beam is typically first determined by means of a rendering or another light propagation calculation software, for example, from a computer model of a fictitious object or by means of a desired beam path pattern. From the fictitious object beam and an also fictitious reference beam defined as computer data, the interference pattern of the two beams is calculated. The resulting interference pattern is normally quantized with respect to phases as well as amplitudes for the purpose of simplifying the production. In the following, the quantized interference will be plotted in the following as a quantized amplitude mask, as a multistep phase relief structure or as a combination of these. If the resulting mask or structure does not have the required high resolution, a photographic reduction takes place. As an alternative, the mask or structure can be produced directly by means of a high-resolution electron beam lithography system or a high-resolution laser beam illumination system instead of the plotting and the reduction.

The holographic elements mentioned in the application having an ellipsoid-type virtual shape can be produced preferably in a computer-aided manner.

The preceding description illustrates that the term "virtual object" has a limiting effect with respect to the case of a holographic element produced in a computer-aided manner, because multiple refraction, diffraction and reflection characteristics which correspond to no real object can be holographically imaged. In order to counteract this undesirable limitation, it is explicitly pointed out here that a holographic element may have any holographic content, even if this holographic content for reasons of clarity is called a "virtual object".

2.1.3 Single-Color and Multicolor Embodiment

Since the interference pattern recorded in a hologram exercises a refraction effect only on those light beams whose wavelength, phase and angle of incidence fit the interference pattern as a key fits a lock, simple holograms essentially have a transparent effect. This is advantageous for the present invention particularly when the holographic element is to be placed in front of the eye.

If a hologram is recorded by means of the light of a single wavelength, the hologram can exercise a refraction essentially only on light of the same wavelength. In the application, this is called a refraction "at a discrete wavelength".

As an alternative, the holographic element according to the invention can refract light "at several discrete wavelengths". This can be achieved in two basically different manners.

On the one hand, several holographic recordings can be made successively by means of the same photo material at respectively different wavelengths but under otherwise identical circumstances. This results in a single hologram which is capable of imitating the refraction characteristics of a single object at several discrete wavelengths.

On the other hand, several holographic recordings can be made successively at respectively different wavelengths but under otherwise identical circumstances, the photo material being exchanged after each recording. The individual recordings can later be merged in layers in order to produce an entire hologram which can imitate the refraction characteristics of a single object at several discrete wavelengths. However, it is difficult to hold the register during the merging.

Analogously, holographic recordings of different objects can be recorded at respectively different wavelengths in a single, as required, multilayer hologram.

The fact that holographic elements generally have a pronounced wavelength selectivity may also be disadvantageous for the information system according to the invention. This is particularly so when a polyspectral image is to be detected by way of a holographic element.

In the case of a projection to be perceived by a person, the known color addition of light of different wavelengths based on the human perception takes place which permits, for example, the implementation of a full-color picture from the discrete primary colors red, and blue. The reversed conclusion that a full-color image can be "reduced" in correspondingly discrete color components generally does not apply. The customary every-day devices which appear to operate according to this principle, detect not only light of a discrete wavelength but light of an entire spectral range.

The underlying problem can be imagined more easily when using an analogy. A typical scene radiates polyspectrallight. In this case, individual photons of a respective discrete wavelength, which corresponds to a respective discrete frequency, are emitted. This is analogous to the polyspectral sound of a symphony orchestra. Imagine how unbearable the music would be if you could perceive only sounds of the precise frequencies of 440 Hz (the concert pitch A), 550 Hz (a major third over it) and 660 Hz (a fifth over the A). The effect would be even more drastic if the first violin had tuned his violin by means of a tuning fork of the 441 Hz frequency against the international standard. He would then experience nothing but silence.

Fortunately, nature is not as selective as a symphony orchestra with respect to the used frequencies. A typical scene beams photons of countless frequencies. In addition, a holographic element can also exercise its light refracting characteristic, which is in a certain range about the wavelength of the light used for the production, on light beams. However, since this range is typically very narrow, light refraction in this range is called light refraction "at a discrete wavelength" in the application.

The number of the holographic elements necessary for a sufficient polyspectrallight detection therefore depends on the goal of the light detection. According to the invention, a holographic element is therefore provided which refracts light at one or several discrete wavelengths, that is, at fewer than 20, fewer than 10 or fewer than 5 discrete wavelengths. If too many holographic recordings are recorded in a single holographic element, this results in a mutual impairment of their effect.

2.2 Markings

A holographic element according to the invention preferably has markings (at least two areas of different optical characteristics). When light is detected by way of such an area as well as by way of at least one such optically different area, the respectively detected light parameters may have differences which are caused by the marking. Since the respective areas of the marking preferably have predetermined optical characteristics, which influence the light incident on them in a correspondingly predetermined manner, the presence of a marking can be clearly determined by means of the detected light. Likewise, a parameter of the detected light can be measured in relation to a predetermined influencing of this parameter because of the marking.

Thus, markings may have different purposes, such as calibration of a parameter of the projected or detected light, and measuring, adjusting and/or calibrating one or more components, particularly of a light guiding device of the information system according to the invention.

An implementation of the markings by means of the holographic element offers many advantages. Mainly, complex, optically very valuable markings can thereby be produced in a cost-effective manner. In addition, it may be advantageous that, as a result of their implementation in the holographic element, the markings may be in a direct relationship with a significant light guiding device of the information system. Furthermore, complex markings can be holographically implemented which could not be implemented by means of other devices, or only to a very limited extent. Not last, holographic markings, because of their nature, are wavelength-selective, angle-selective and/or phase selective and therefore predestined for use characterizing or selective elements. Among other things, markings can be implemented in the holographic element which influence, for example, only invisible infrared light.

The markings may have any shape. An implementation in the shape of a reticule would be meaningful, for example, when the flags are used as reference coordinates.

The markings may have any optical characteristics. A marking suitable for the calibration of a projection device and scanning device combination could, for example, have reflective areas which direct the beams projected by the projection device completely onto the scanning device. Other areas could direct the projection beam such that it definitely does not arrive in the scanning device. A scanning device which is advantageous in this context and has several detector areas is described in Section 3.4 ("Special Scanning Devices").

2.3 Ellipsoid-Type Embodiment

The holographic element preferably has light-refracting characteristics at one or several discrete wavelengths along a partial area of a virtual ellipsoid, the holographic element and the partial area preferably being disposed in front of an eye and one of the focal points of the virtual ellipsoid coinciding with the optical center of the eye. Preferably, the other focal point of he ellipsoid spatially coincides with an optical output point of a projection device or light guiding device coupled thereto and/or with an optical input point of a scanning or light guiding device coupled thereto.

When the virtual focal points of the virtual ellipsoid spatially coincide with the optical center of the eye and an optical output point of a projection device or an optical output point of a light guiding device coupled thereto, an advantageous beam path for the projection is obtained if the refraction characteristics of the virtual ellipsoid are selected correspondingly.

If the virtual focal points of the virtual ellipsoid spatially coincide with the optical center of the eye and an optical input point of a scanning device or an optical input point of a light guiding device coupled thereto, an advantageous beam path for the scanning is obtained if the refraction characteristics of the virtual ellipsoid are selected correspondingly. This applies to the scanning from the eye as well as to the scanning from the environment.

The implementation of a light-refracting partial area of a virtual ellipsoid by a holographic element particularly has the advantage that the holographic element itself need not be developed in the shape of an ellipsoid. This is particularly advantageous when the information system of the invention is implemented in the form of spectacles. In addition, the light refraction caused by the holographic element can be implemented in a wavelength-selective fashion, so that the holographic element is transparent at the remaining wavelengths. Similarly, for example, the ellipsoid of a holographic element to be assigned to a scanning device with respect to the wavelength may have different dimensions, a different position, and/or a different orientation than the ellipsoid of a holographic element to be assigned to a projection device with respect to the wavelength. This would be meaningful, for example, in the case of a nonconfocal arrangement of a scanning device and a projection device.

2.3.1 Internally Reflective

The holographic element preferably has light refracting characteristics at one or several discrete wavelengths which correspond to a reflection on the concave side of an area constructed according to the curvature of a rotationally symmetrical ellipsoid.

According to the following explanation, such an embodiment of the holographic element can be advantageously used for a projection of light into the eye or for a scanning of light from the eye.

If the eye is considered to be an idealized optical system, in which incident light always runs through a common optical center, and if the optical output of a projection device or a light guiding device coupled thereto and/or the input of a scanning device or of a light guiding device coupled thereto are considered to be a point light source or a point detector, beams originating from one of the points would always run to the other point if these points correspond to the respective focal points of an internally reflecting rotationally symmetrical ellipsoid.

By means of a holographic element, the reflection characteristics of such an ellipsoid can be emulated without the requirement that the holographic element has the external shape of such an ellipsoid. Furthermore, by means of the knowledge of the shape of the ellipsoid, from the angle of incidence of the light on the detector point, the "angle of reflection" of the light from the eye can be determined, or from the projection direction, the angle of incidence on the eye can be determined.

2.3.2 Perpendicularly Reflective

The holographic element preferably has light-refracting characteristics at one or several discrete wavelengths which correspond to a refraction on the concave side of an area constructed according to the curvature of a rotationally symmetrical ellipsoid, which refraction corresponds to a reflection at a respective conical area rotationally symmetrical about the axis of rotation of the ellipsoid, the conical area being perpendicular to the ellipsoid at the site of the refraction According to the above explanations, such an embodiment of the holographic element can advantageously be used during a scanning of light from the field of vision of an eye.

If the eye is considered to be an idealized optical system, in which incident light always runs through a common optical center, and if the input of a scanning device or a light guiding device coupled thereto is considered to be a point detector, beams directed at the one point would always run through the other point if these points correspond to the respective focal points of an above described rotationally symmetrical ellipsoid of a holographic element implemented in such a manner. By means of the knowledge of the shape of the ellipsoid, the "angle of incidence" of the light onto the eye can be determined from the angle of incidence of the light on the detector point.

Analogously, such a holographic element in the secondary sense of the invention could advantageously be used for projecting light from an output point of a projection device or a light guiding device coupled thereto into the field of vision of the eye.

While such a holographic element would be difficult to implement by holographic recording of a real object, such a holographic element can be implemented in a computer-aided manner. The result is an easily reproducible optical element capable of refracting light beams directed onto an eye while maintaining a clear assignment to the angle of incidence onto a common point. In addition, by means of a holographic element, the indicated refraction characteristics can be emulated without any effect on the external shape of the holographic element.

A special advantage of an embodiment of the holographic element described here (for the purpose of the present explanation: "HE1") is its possible combination with a holographic element ("HE2") according to the preceding section. If the respective ellipsoids are uniform and virtually identical with respect to location, and HE1 is used for the refraction of light beams ("L1 beams") incident directly from the environment, while HE2 is used for the refraction of light beams ("L2 beams") between the eye and the projecting or light-detecting components of the information system, those L1 beams directed at HE1 and those L2 beams directed at/from HE2 are coaxial which have the same beam path between HE 1 or HE2 and the respective projection, scanning or light guiding device. This advantage will be explained in detail below with reference to the drawings.

2.3.3 Scan Angle Enlargement or Reduction

The holographic element preferably has light-refracting characteristics at one or several wavelengths along a partial area of a virtual ellipsoid, the holographic element being used for enlarging or reducing the scan angle of a projection and/or scanning device or of a light guiding device coupled therewith.

If the projection or scanning direction of a projection or scanning device changes with time, a scan angle is obtained, that is, an angle measured between respective projecting or scanning directions. Such a change of the projecting or scanning direction frequently takes place by a controllable light guiding device which has a limited scan angle range or a limited scan angle resolution.

In the case of a non-spherical ellipsoid, the angle between two light beams originating from a focal point of the ellipsoid, which are reflected on the internal surface of the ellipsoid, is not equal to the angles between these two light beams when arriving on the other focal point of the ellipsoid.

Correspondingly, a holographic element according to the preceding sections can advantageously be used for enlarging or reducing the scan angle of a projection and/or scanning device or a light guiding device coupled thereto. In addition, it is advantageous that the physical shape of the holographic element definitely does no have to coincide with the shape of the recorded object, that is, the "virtual" shape of the holographic element. Correspondingly, the dimensions of the ellipsoid can be freely selected according to the system requirements.

2.4 Adjustment

The information system according to the invention preferably has a holographic element with light-refracting characteristics at one or several discrete wavelengths, in which case the position of the holographic element and/or of the holographic virtual object can be changed with respect to a part of the information system. This applies particularly in the case of a holographic element with light-refracting characteristics at one or several discrete wavelengths along a partial area of a virtual ellipsoid.

The preceding description illustrates that a special positioning of the holographic element and/or of the holographic virtual object, particularly with respect to an eye, a scanning device, a projection device and/or a light guiding device coupled thereto can achieve considerable advantages.

However, the information system is normally not fixed at the head such that an exact positioning of the holographic element or of the holographic virtual object with respect to the eye could always be ensured. In addition, the information system will normally detect light from both eyes or project light into both eyes. However, the distance between both eyes may vary considerably among different people.

For this and other reasons, it is advantageous for the position of the holographic element and/or of the holographic virtual object to be variable with respect to a part of the information system. The position change can take place in a one-dimensional, two-dimensional or three-dimensional manner. However, the position of the holographic virtual object is preferably unchangeable with respect to a scanning device, a projection device and/or a light guiding device coupled therewith.

2.4.1 Mechanical or Manual Adjustment

Preferably, the position of the holographic element and therefore the position of the holographic virtual object with respect to a part of the information system can be changed mechanically and/or manually.

A mechanical positioning could be triggered by the user or carried out automatically by the information system according to the invention, if required, and/or during the switching-on. In this case, for example, various positions could be tried out and the best functioning position could be identified by the user or recognized by way of the scanning device. The information system preferably comprises servomotors, piezo elements or other suitable mechanical devices for the positioning.

Positioning could be carried out manually according to the random principle, or for example, by means of visible positioning aids that indicate the correct position of the information in front of the eye.

The manner of change depends considerably on the design of the information system and can therefore generally not be further specified here. In the case of an information system further developed in the form of spectacles, the change could, for example, consist of the fact that a left and a right half of the spectacles are displaced with respect to one another. Likewise, "spectacle lenses" constructed as a holographic element could be displaced with respect to the frame.

2.4.2 Optical or Electronic Adjustment

Preferably the position of the virtual object is optically quasi changeable with respect to a part of the information system. As an alternative, the position of the holographic virtual object can preferably be changed electronically with respect to a part of the information system.

A quasi change of the position of the holographic virtual object could by implemented by a holographic element which has several, respectively displaced recordings of the object under respectively different holographic conditions.

For example, the object could be recorded several times at different wavelengths and in different positions. When the wavelength of the light detected or projected by way of the holographic element is then correspondingly changed, the light is virtually refracted at a differently positioned holographic virtual object, which corresponds to a position change of the holographic virtual object.

An electronic change of the position of the holographic virtual object requires the use of an electro-holographic element, which could, for example, have several, respectively displaced recordings of the object, which recordings can be called in each case by the application of a suitable voltage.

A positioning of the holographic virtual object, as described above, could be triggered by the user or automatically carried out by the information system according to the invention, as required, and/or could be carried out during the switching-on. Different positions could, for example, be tried out and the best functioning position could be identified by the user or recognized by way of the scanning device.

The above-mentioned optical and electro-holographic methods for changing the position of a holographic virtual object could be analogously used for changing the light refraction characteristics of the holographic element in a predetermined manner.

2.5 Beams Perpendicular to the Eye

The information system according to the invention preferably comprises a holographic element which is capable of directing the light beams according to their reflection angles from a projection device or a light guiding device coupled therewith perpendicularly onto a respective region of the eye and/or light beams, which emerge perpendicularly from a respective region of the eye or are reflected back, with a corresponding angle of incidence into a scanning device or a light guiding device coupled therewith.

The advantages and conceivable design criteria of such a holographic element were discussed in detail in Section 1.6.2. Particularly a holographic element according to Section 2.3 may be suitable as such a holographic element with a corresponding positioning and curvature of the virtual ellipsoid.

3 Projection and Scanning

In the following, several preferred characteristics will be described which relate to the projection, the scanning as well as the pertaining devices.

3.1 Beam Diameter

The lens system of the projection or scanning device is preferably designed such that a light beam with a predetermined or determinable beam diameter is projected or detected. This (pre)determination of the beam diameter can be implemented by way of a suitable light shaping device, for example, by way of a focusing or modulating device.

The determination of the beam diameter, for example, in connection with a determination of the projecting or scanning direction, permits a spatial targeted projection or scanning.

Here, as well as at other points of the specification, the term "narrow light beam" preferably is a light beam according to German Patent Document DE 101 27 826 which is projected into the eye with a low divergence, low convergence or coherently such that, at the air-eyeball transition, particularly at the air-cornea transition, the light beam has a diameter which is insignificant in comparison to the diameter of the pupil (for example, less than 100 μm, less than 50 μm, less than 10 μm, or even less than 5 μm).

With respect to the system, the use of a narrow light beam has the advantage that the beam path of the entire light beam has approximately the same beam path as the main beam assigned to the light beam. This means that the refraction of the light beam at an uneven surface leads to no significant macroscopic change of the divergence, the convergence or the coherence of the light beam. This applies to the projection as well as to the scanning.

By using a projection device beaming at a correspondingly high light intensity, such as an LED or a laser diode, during a projection, despite the narrow light beam, a sufficient amount of light can easily be projected onto the part of the eye to be illuminated.

3.2 Focusing

The projection and/or scanning device preferably has a focusing device by means of which the projected or detected beam can be focused.

As described above, a focusing device can be used for a spatial targeted projection or scanning. In particular, a focusing device can be used for sharply imaging objects on the detecting elements of the scanning device, which objects are situated at a distance from the scanning device, which can be determined by way of the focusing device, along the scanning beam path. Analogously, a focusing device can focus projected light beams on objects, that is, converge them, which are situated at a distance determinable by means of the focusing device, along the projection beam path from the projection device.

According to the invention, a focusing device can therefore, for example, be used for projecting light to a defined part of the eye or detect it from a defined part of the eye. This can particularly be used for the targeted scanning of one of several ocular structures "situated behind one another", which applies, for example, to the frontal cornea surface, the rear cornea surface and the retina. This analogously applies to the projection.

In the case of very narrow, quasi convergent light beams, whose beam diameter hardly changes in the course of the beam path, a focusing is expedient to a limited extent.

3.3 Common Beam Path

The information system according to the invention preferably comprises a projection device and a scanning device which have a common beam path. The projection device and the scanning device preferably are arranged in a confocal manner, for example, on respective sides, of a splitter mirror.

If a projection device and a scanning device have a common beam path, as a result of the reversibility of a light beam, they can jointly use a possibly existing light guiding device. This represents a simplification of the information system.

Nevertheless, a common beam path ensures that projected light beams, which are beamed back against the projection direction, for example, from the eye, are, as it were, "automatically" guided to the scanning device. As a result, a high-expenditure "synchronization" of a light guiding device assigned to the scanning device and of a light guiding device assigned to the projection device can be eliminated.

If a confocal arrangement of the projection and of the scanning device is implemented by way of a splitter mirror or a similar beam-splitting element, it is advantageous to give the scanning beam priority. This is particularly advantageous when scanning weakly radiating objects, such as the retina. The splitter mirror preferably guides more than 95% of the scanning beam in the direction of the scanning device. Instead of 95%, for the benefit of the projection beam, only more than 90%, 85% or even 80% of the scanning beam can be transmitted in the direction of the scanning device by the splitter mirror. The resulting weakening of the projection beam is normally insignificant, because this can be compensated by a corresponding increase of the intensity of the light beam projected by the projection device. The maximal intensity of the projection beam is typically determined by the photonic maximum stressing capacity of the eye tissue. If an increase of the intensity of the projection beam in the case of a desired implementation of the information system is not expedient, any other light splitting ratio of the splitter mirror can be selected.

3.4 Special Scanning Devices

The information system according to the invention preferably has a scanning device which detects light in at least two adjacent areas which are preferably situated concentrically around one another.

By means of a scanning device, which detects light in at least two adjacent areas which are not situated around one another, it can be determined into which direction an incident light beam is moving and/or when the light beam leaves a certain area. This is achieved, for example, by a comparison of the intensity of the light beam incident on the respective area.

By means of a scanning device, which detects light in at least two areas situated concentrically around one another, it can be determined, as described above, whether an incident light beam is moving in the direction of the detector center or away from the detector center and/or when the light beam leaves a certain area.

Since the above-mentioned recognitions permit a localizing of the beam end point, they can, for example, in the knowledge of the geometrical arrangement of the scanning device, the light source and the light guiding devices participating in the beam path, advantageously be used for the calibration and/or control of the light guiding devices of he information system.

In particular, a scanning device, which detects light in at least two areas situated concentrically around one another, can advantageously be used for locating or positioning a beam end with respect to two coordinates.

3.5 Adjustment

Analogous to the measures described in Section 2.4, the position, orientation and/or the optical characteristics of other optical devices included in the information system according to the invention, particularly possibly light guiding devices, can be changed.

3.6 Scanner Device

The projection or scanning device preferably comprises a controllable light guiding device which changes the direction into which a light beam is projected or from which direction a light beam is detected. Such light guiding devices, partially known under the name "scanners", are known to a skilled person and comprise many different devices. These include, for example, electromechanical, acousto-mechanical and similar movable mirror devices, electro- and acousto-optical modulators, electro-holographic elements, movable light guiding arrangements, etc.

3.7 Special Light Sources

The projection device preferably comprises a laser which can project light at one or several of several evenly distributed wavelengths.

Recently, lasers have been developed which have evenly distributed modes. Such a laser is extremely suitable for being used in combination with a holographic element which refracts light at several regularly distributed discrete wavelengths.

Other objects, advantages and novel features of the present invention will become apparent from the following detailed description of the invention when considered in conjunction with the accompanying drawings.

DETAILED DESCRIPTION

In the description of the figures, similar or identical objects are marked by reference numbers ending in a similar or identical manner. Many of the illustrated objects have symmetrical or complementary components, which are differentiated by an additional letter, for example, "L" for left and "R" for right, after the reference number. If a statement relates to each individual component of such a symmetrical or complementary grouping, the additional letter is omitted in some cases for reasons of clarity.

Figure 1:
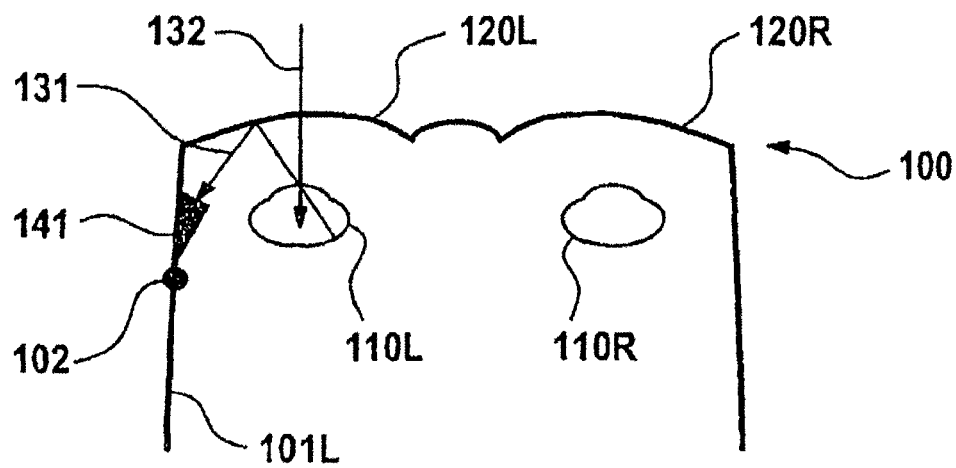
FIG. 1 is a schematic representation of a scanning information system according to a first embodiment.

FIG. 1 is a schematic representation of a scanning information system 100 according to a first embodiment of the invention, in which the scanning information system 100 is designed in the shape of spectacles 100 that have two holographic elements 120R, 120L in the form of spectacle lenses 120R, 120L arranged in front of each 110R, 110L. On the left bow 101L of the spectacles 100, a scanning device 141 is fastened which is capable of detecting light beams 131 coming from the eye 110. The scanning device 141 preferably comprises a light guiding device (not shown) such as a scanner device, which determines the momentary detection direction of the scanning device 141 and changes time, according to a predetermined scan pattern. Naturally, an additional scanning device (not shown) could also be fastened on the right bow 101R. The light beam 132 indicates that light beams 132 originating from the environment are allowed to pass unhindered by the holographic element 120.

In this embodiment, the holographic element 120 only has the purpose of refracting light beams 131 coming from the eye 110 into the direction of the scanning device 141. The wavelengths to be refracted depend on the desired detection.

If, for example, an image of the retinal structure is to be detected, a light refraction of the holographic element at a discrete wavelength in the infrared range would be useful. If an image of the structure of the iris is to be detected, a light refraction of the holographic element at several discrete wavelengths in the visible range would make sense.

In order to ensure a predetermined relative arrangement of the scanning device 141 with respect to the holographic element 120, the hinge 102 may, for example, be arranged behind the scanning device 141 for the folding together of the spectacle frame.

Figure 2:
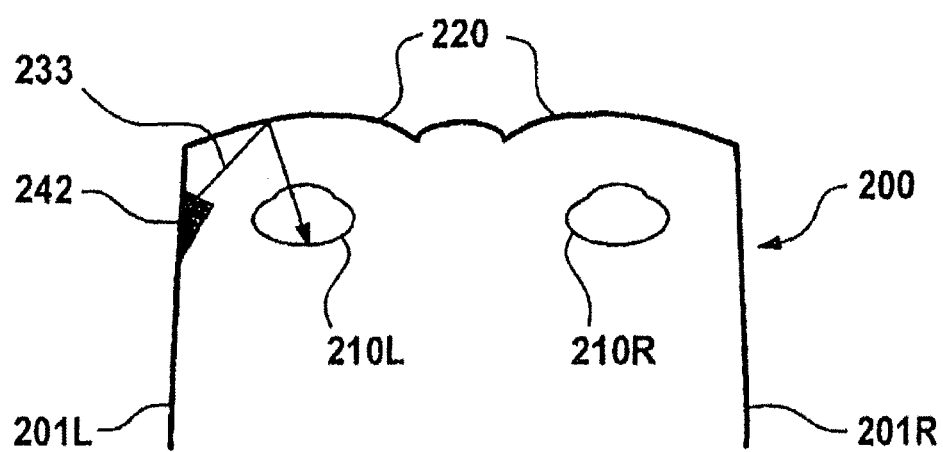
FIG. 2 is a schematic representation of a projecting information system according to a second embodiment.

FIG. 2 is a schematic representation of a projecting information system 200 according to a second embodiment, in which the projecting information system 200 is designed in the form of spectacles 200 having two holographic elements 220 constructed as spectacle lenses 220 each arranged in front of an eye 210. On the left bow 201 L of the spectacles 200, a projection device 242 is fastened which is capable of projecting light beams 233 onto or into the eye 210. The projection device 242 preferably comprises a light guiding device (not shown), for example, a scanner device which determines the momentary projecting direction of the projection device 242 and changes it with respect to time according to a predetermined projection pattern. Naturally, an additional projection device, which is not shown, could also be fastened on the right bow 201R.

In this embodiment, the holographic element 220 is used only for refracting light beams 233 projected by the projection device 242 in the direction of the eye 210. The wavelengths to be refracted by the holographic element 220 will therefore preferably be adapted to the wavelength of the projection beams 233.

Figure 3:
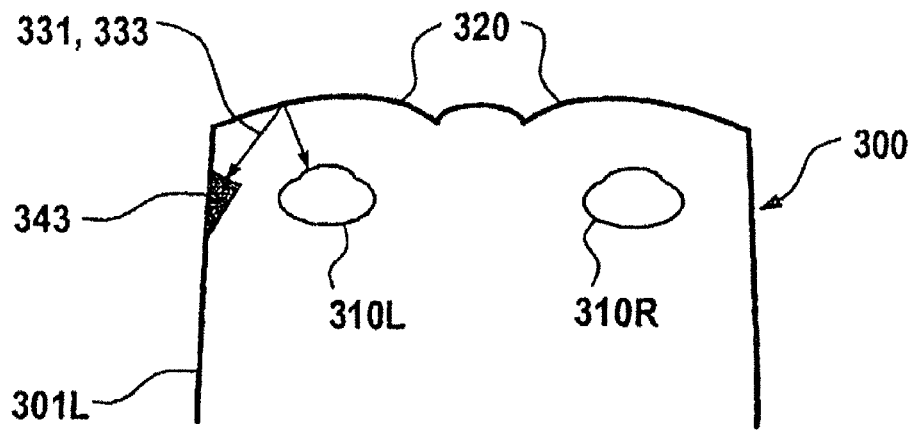
FIG. 3 is a schematic representation of an information system according to a third embodiment.

FIG. 3 is a schematic representation of an information system 300 according to a third embodiment, in which the information system 300 is designed in the form of spectacles 300, with two holographic elements 320 designed as spectacle lenses 320 which are each arranged in front of an eye 310. At the left bow 201 L of the spectacles 200, a combined projection and scanning device 343 is fastened, which is capable of projecting light beams 333 onto or into the eye 320 as well as also detecting light beams 331 coming from the eye 310. The projection device 343 preferably comprises a light guiding device (not shown), such as a scanner device, which projects the momentary projecting direction of the projection device 343 and changes it with respect to time according to a predetermined projection pattern.

Such an information system 300 could be used, for example, for illuminating the retina of the eye 310 in an actively point-focal manner, and to detect the light 331 reflected in by the retina for the purpose of recognizing structures of the retina.

In this embodiment, the holographic element 320 refracts the light 333 projected by the projection device 343 as well as the light 331 detected by the scanning device 343.

Figure 4:
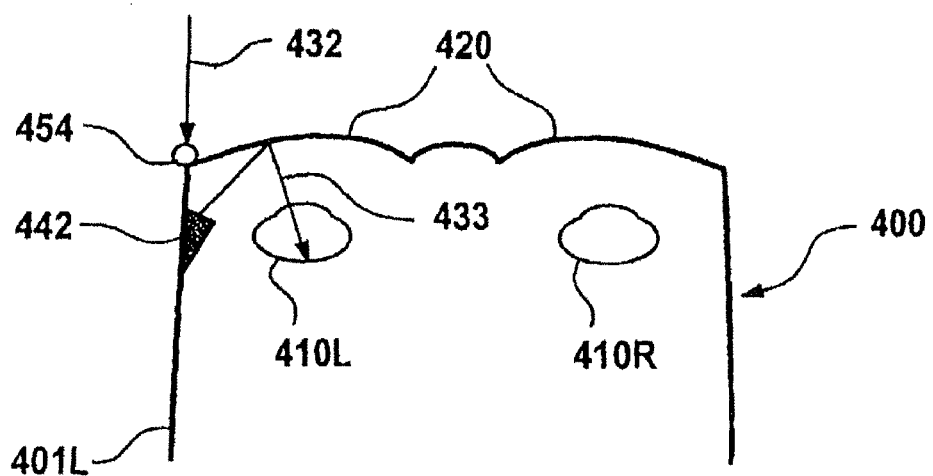
FIG. 4 is a schematic representation of an information system according to a fourth embodiment.

FIG. 4 is a schematic representation of an information system 400 according to a fourth embodiment, in which the information system 400 is designed in the shape of spectacles 400, with two holographic elements (spectacle lenses) 420 which are each arranged in front of an eye 410. At the left bow 401 L of the spectacles 400, a projection device 442 is fastened which is capable of projecting light beams 433 onto or into the eye 410. In this case, the holographic element 420 refracts the light 433 projected by the projection device 442 in the direction of the eye 410. Furthermore, a scanning device 454, such as a camera 454, is arranged on the forward part of the left bow 401 L, which camera 454 detects light beams 432 from the environment.

Such an information system 400 could be used, for example, for projecting information in correlation with the perceived field of vision of the eye 410 into the eye 410.

Figure 5:
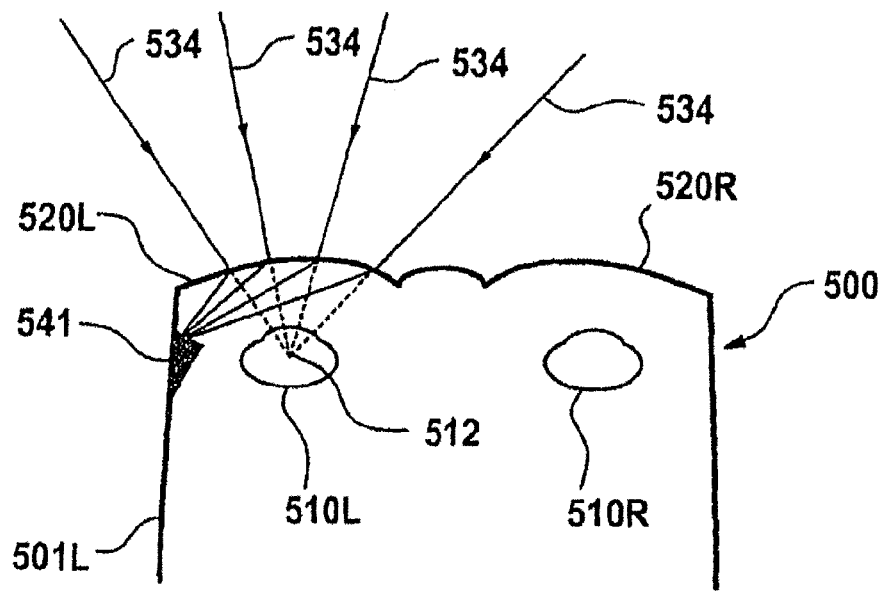
FIG. 5 is a schematic representation of an information system according to a fifth embodiment.

FIG. 5 is a schematic representation of a fifth embodiment of the information system 500 according to the invention, in which the information system 500 is designed in the shape of spectacles 500 with two holographic elements (spectacle lenses) 520 which are each arranged in front of an eye 510. A scanning device 541 is fastened on the left bow 501L of the spectacles and is capable of detecting light beams 532 from the environment which were refracted on it by the holographic element.

The holographic element 520 is constructed such that light beams 534 from the environment directed onto the optical center 512 of the eye 510 are refracted onto a common point at which the optical input of the scanning device 541 is arranged. The light beams 534 are preferably refracted by the holographic element 520 such that their respective angle of incidence onto the scanning device 541 supplies clear information on the angle of incidence of the respective light beam onto the holographic element 520. A conceivable embodiment of such a holographic element 520 is described in Section 2.3.2.

Such an information system 500 could, for example, be used for obtaining information with respect to the field of vision perceived by the eye 510.

Figure 6:
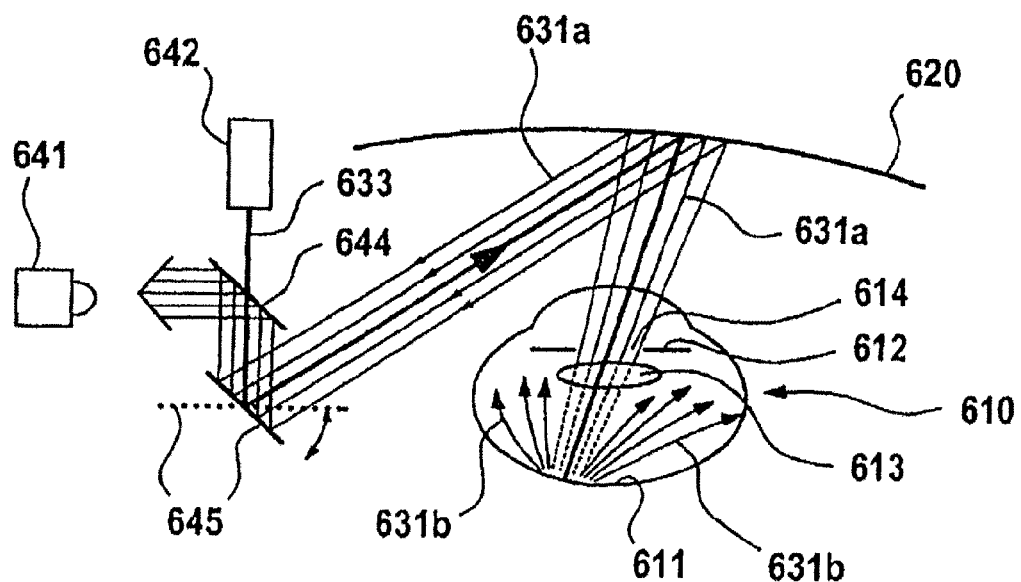
FIG. 6 is a schematic view of a detail of an information system according to a sixth embodiment.

FIG. 6 is a schematic view of a detail of an information system 600 according to a sixth embodiment, which has a projection device 642, a scanning device 641, a light guiding device 645 and a holographic element 620 arranged in front of an eye 610. The projection device projects a light beam 633, which partially passes through a splitter mirror 644 and is directed by the light guiding device 645 by way of the holographic element 620, onto the retina 611 of the eye 610. There, the projected light beam 633 is scattered back into different directions as reflex light rays 631. Some 631a of the reflex light rays 631 are focused by the lens 613 of the eye 610 such that they 631a beam almost parallel but opposite to the projection beam 633 through the pupil 614. Subsequently, these reflex light rays 631a are refracted by the holographic element 620, directed by the light guiding device 645, partially reflected at the splitter mirror 644 and detected by the scanning device 641. Other rays 631b of the reflex light rays 631 are prevented from emerging from the eye 610, for example, by the iris 612 of the eye 610.

In this embodiment, the projection beam 633 and the scanning beam 631a share a common beam path. Two light guiding devices 645 are therefore not required. Since the retina reflects only approximately 4% to 10% of the incident light, a splitter mirror 644 is preferably selected which reflects the scanning beam 631a almost completely in the direction of the scanning device 641 and correspondingly weakens the projection beam 633. In order to compensate this weakening of the projection beam 633, the intensity of the projection beam 633 is increased correspondingly. The maximal intensity of the projection beam 633 is typically determined by the maximal stressing limit of the retina 611.

In such an embodiment, the limitation of the scanned area can take place by way of a corresponding spatial limitation of the area illuminated by the projection beam 633. A limitation of the beam paths along which a light beam 631a can be beamed back from the retina 611 to the scanning device 641 automatically takes place through the pupil 614.

Figure 7A:
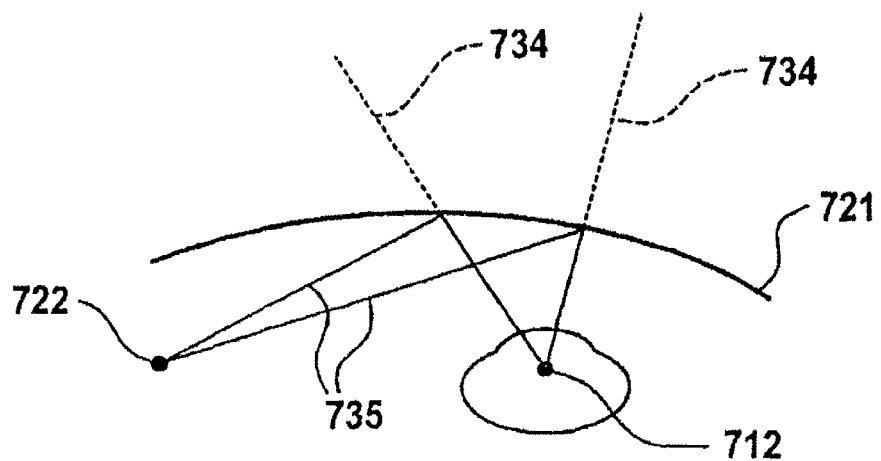
FIG. 7A is a schematic top view of an information system according to a seventh embodiment.
Figure 7B:
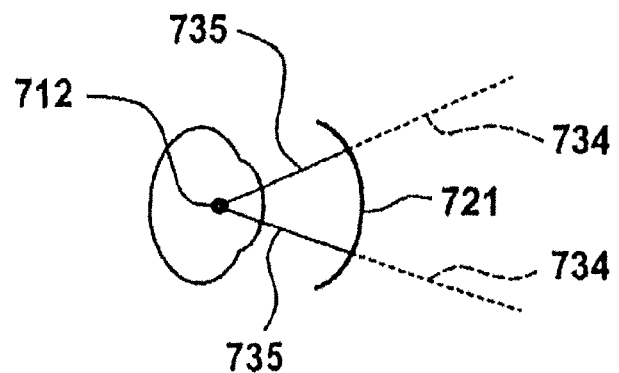
FIG. 7B is a schematic lateral view of an information system according to a seventh embodiment.

FIGS. 7A and 7B, are, respectively, schematic top and lateral views of an information system according to a seventh embodiment of the invention, in which the holographic element refracts light along a virtual ellipsoid area 721.

FIGS. 7 and 7B illustrate schematically how light beams 734, which are directed onto the optical center 712 of the eye and are reflected on the virtual ellipsoid area corresponding to a reflecting area situated at the reflection point perpendicular to the ellipsoid area 721, run through a common point 722 which is also jointly passed by those beams 735 which, originating from the optical center 712 of the eye, are reflected on the interior side of the ellipsoid area 721 in a reflective manner.

Figure 8A:
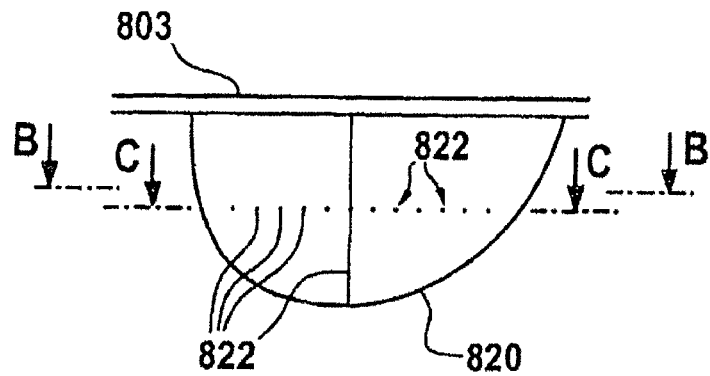
FIG. 8A is a schematic frontal view of an information system according to an eight embodiment.
Figure 8B:
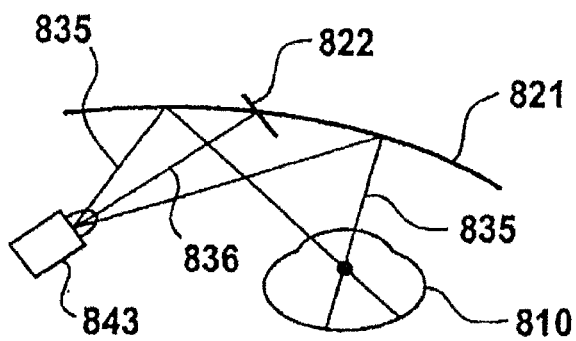
FIG. 8B is a schematic top view of an information system according to an eighth embodiment along sectional line B in FIG. 8A.
Figure 8C:
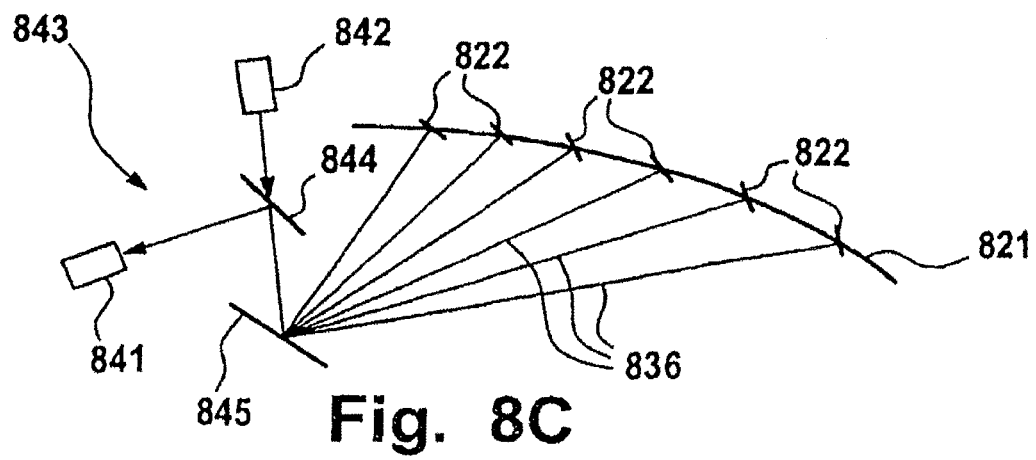
FIG. 8C is a schematic top view of an information system according to an eighth embodiment along sectional line C in FIG. 8A.

FIG. 8A is a schematic frontal view onto an information system according to an eighth embodiment, while FIG. 8B is a schematic top view along sectional line B in FIG. 8A, and FIG. 8C is a schematic top view along sectional line C in FIG. 8A.

FIG. 8A illustrates a holographic element 820 constructed in the shape of spectacles 820 which is fastened to a spectacle frame 803. The holographic element 820 indirectly has markings 822, which preferably are not generally visible but are holographically implemented, so that they influence only light of a certain wavelength, phase and angle of incidence.

FIG. 8B illustrates a combined projection and scanning device 843 which projects light beams 835, 836 on a virtual holographic object 821 having flags 822. Projected light beams 835, which do not impinge on the flags, are refracted by the virtual holographic object 821 in the direction of the eye 810. Projected light beams 836, which do impinge on the markings, are reflected back by the holographic object 821 along the projection beam path and can therefore be detected by the combined projection and scanning device 843. Thus, the projecting direction as well as the signal level, which is to be expected on the basis of a projection and a subsequent detection of the projected light beam, can be checked. In addition, the detected markings 822 can be used as reference coordinates when obtaining information or when providing information.

FIG. 8C illustrates the possible construction of a combined projection and scanning device 843 which, similarly to FIG. 6, comprises a projection device 842, a scanning device 841, a splitter mirror 844 and a light guiding device 845. By means of the light beams 836 projected analogously to FIG. 8B and reflected back by the markings 822 of the virtual holographic object 821, for example, the adjusting angle of the light guiding device 845 can be checked. In addition, the detected markings 822 can be used as reference coordinates when obtaining information or when providing information.

FIGS. 9A-9E are schematic views of the method of operation of a scanning device 941 according to a ninth embodiment, comprising two detecting areas 941a, 941b which are situated concentrically around one another.

Figure 9A:
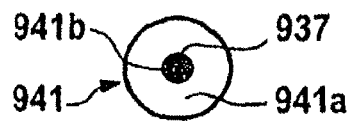
FIGS. 9A-9E are schematic views of the method of operation of a scanning device according to a ninth embodiment.
Figure 9B:

In FIG. 9A, only area 941b detects light. The beam end therefore has to be situated entirely within area 941b. Subsequently, both areas 941a and 941b detect light according to FIG. 9B. The beam end clearly moves away from area 941b. The moving direction is unknown.

Figure 9C:
Figure 9D:
Figure 9E:

Subsequently, only area 941a detects light according to FIG. 9C. The beam end therefore has to be situated entirely within area 941a. Subsequently, according to FIG. 9D, area 941b detects no light, while area 941a detects less light then before. The beam end clearly moves relative to the scanning device 941. The moving direction is unknown. In FIG. 9E, neither area 941a nor area 941b detects light. The beam end is therefore clearly situated outside areas 941a and 941b.

Such a scanning device 941 can advantageously be used for locating or positioning a beam end with respect to two coordinates.

FIGS. 10A-10D are schematic views of the method of operation of a scanning device 104 according to a tenth embodiment, in which the scanning device 1041 detects light in two adjacent areas 1041a, 1041b.

Figure 10A:
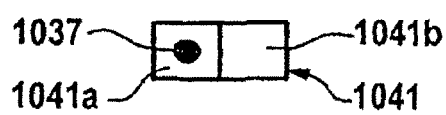
FIGS. 10A-10D are schematic views of the method of operation of a scanning device according to a tenth embodiment.
Figure 10B:
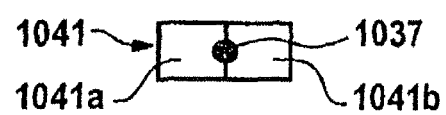

In FIG. 10A, only area 1041a detects light. Thus the beam end has to be situated at least partially in area 1041a. Subsequently, both areas 1041a and 1041b detect light according to FIG. 10B. The beam end clearly moves away from area 1041a in the direction of area 1041b.

Figure 10C:
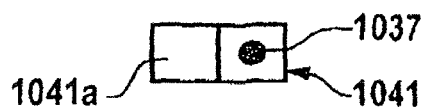
Figure 10D:
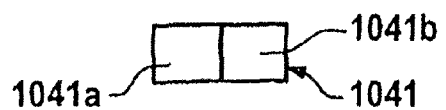

Subsequently, only area 1041b detects light according to FIG. 10C Thus, the beam end has to at least partially be situated within area 1041b and must have moved farther into the previously defined direction. Finally, according to FIG. 10D, area 1041a nor area 1041b detects light, without area 1041a having detected light in the interim. The beam end therefore has clearly moved away from the scanning device 1041 into the previously defined direction.

A scanning device 1041 of this type can advantageously be used for determining into which direction an incident light beam end is moving and/or when the light beam end is leaving a defined area.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

We claim:

1. An information system for providing information with respect to an eye, the system comprising:
    at least a first optical projection device configured to project infrared light into an environment in a field of vision of said eye;
    at least one camera configured to detect the infrared light reflected back from the environment;
    a sensor system configured to obtain information from the environment based on triangulation of the infrared light reflected back from the environment;
    spectacles including a holographic element disposed in front of said eye; and
    at least a second optical projection device configured to project light via the holographic element into said eye in correlation with the obtained information;
    wherein the holographic element has light-refracting characteristics at one or more discrete wavelengths along a partial area of a virtual ellipsoid disposed in front of said eye.

2. The information system of claim 1, wherein a first focal point of the virtual ellipsoid spatially coincides with the optical center of the eye and a second focal point of the virtual ellipsoid spatially coincides with the optical output point of the optical projection device.

3. An information system for providing information with respect to an eye, the system comprising:
    at least a first optical projection device configured to project infrared light into an environment in a field of vision of said eye;
    at least one camera configured to detect the infrared light reflected back from the environment;
    a sensor system configured to obtain information from the environment based on triangulation of the infrared light reflected back from the environment;
    spectacles including a holographic element disposed in front of said eye;
    at least a second optical projection device configured to project light via the holographic element into said eye in correlation with the obtained information; and
    a device configured to detect optical signals and to obtain at least a partial reflex image from said eye.

4. The information system of claim 3, wherein the sensor system is further configured to determine at least one of a position and an orientation of at least one of the information system and the eye with respect to the environment.

5. The information system of claim 3, wherein at least one of a position of a holographic content and light refraction characteristics of the holographic element is electronically changeable.

6. The information system of claim 3, wherein said second optical projection device includes an LED that projects light into the eye via the holographic element.

7. The information system of claim 3, wherein the correlation includes at least one of a time-related correlation, a color-related correlation, a spatial correlation, or a contrast-related correlation.

8. The information system of claim 3, further comprising:
    an analyzing device configured to obtain information about one or more eye structures from the partial reflex image.

9. The information system of claim 3, further comprising:
    an analyzing device configured to obtain information about one or more eye structures from the partial reflex image.

10. An information system for providing information with respect to an eye, the information system comprising:
    a first optical projection device configured to project infrared light into an environment in a field of vision of the eye;
    a camera configured to detect the infrared light reflected back from the environment;
    a sensor system configured to obtain information from the environment based on triangulation of the infrared light reflected back from the environment;
    a first optical element disposed in front of the eye, wherein the first optical element includes a holographic element;
    a second optical projection device configured to project light via the first optical element into the eye in correlation with the obtained information; and
    a device configured to detect optical signals and to obtain at least a partial reflex image from said eye.

11. The information system of claim 10, wherein at least one of the first optical element and a second optical element is disposed in front of the eye.

12. The information system of claim 3, wherein the sensor system is further configured to determine a region of the environment at which a portion of the eye with sharpest vision is momentarily directed.

* * * * *